(12) United States Patent
Golde et al.

(10) Patent No.: US 12,258,395 B2
(45) Date of Patent: Mar. 25, 2025

(54) MATERIALS AND METHODS FOR TREATING STRESS-RELATED DISORDERS AND CANCER

(71) Applicant: UNIVERSITY OF FLORIDA RESEARCH FOUNDATION, INC., Gainesville, FL (US)

(72) Inventors: Todd Eliot Golde, Gainesville, FL (US); Hunter S. Futch, Gainesville, FL (US); Brenda Dawn Moore, Gainesville, FL (US); Benoit Giasson, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1007 days.

(21) Appl. No.: 16/973,502

(22) PCT Filed: Jun. 10, 2019

(86) PCT No.: PCT/US2019/036337
§ 371 (c)(1),
(2) Date: Dec. 9, 2020

(87) PCT Pub. No.: WO2019/241127
PCT Pub. Date: Dec. 19, 2019

(65) Prior Publication Data
US 2021/0371514 A1 Dec. 2, 2021

Related U.S. Application Data

(60) Provisional application No. 62/843,677, filed on May 6, 2019, provisional application No. 62/777,572, filed on Dec. 10, 2018, provisional application No. 62/683,369, filed on Jun. 11, 2018.

(51) Int. Cl.
| | | |
|---|---|---|
| *C07K 16/26* | (2006.01) | |
| *A61K 38/35* | (2006.01) | |
| *A61K 39/00* | (2006.01) | |
| *A61K 47/64* | (2017.01) | |
| *A61K 47/68* | (2017.01) | |
| *A61P 35/00* | (2006.01) | |
| *C07K 16/28* | (2006.01) | |

(52) U.S. Cl.
CPC ............ *C07K 16/26* (2013.01); *A61K 38/35* (2013.01); *A61K 39/001144* (2018.08); *A61K 47/6415* (2017.08); *A61K 47/6847* (2017.08); *A61P 35/00* (2018.01); *C07K 16/2818* (2013.01); *A61K 2039/505* (2013.01)

(58) Field of Classification Search
CPC .... C07K 16/26; C07K 16/2818; A61K 38/35; A61K 47/6415; A61K 47/6847; A61K 2039/505; A61P 35/00
See application file for complete search history.

(56) References Cited

U.S. PATENT DOCUMENTS

| | | |
|---|---|---|
| 3,773,919 A | 11/1973 | Boswell et al. |
| 4,946,778 A | 8/1990 | Ladner et al. |
| 5,139,941 A | 8/1992 | Muzyczka et al. |
| 5,225,539 A | 7/1993 | Winter |
| 5,236,901 A | 8/1993 | Burks et al. |
| 5,252,479 A | 10/1993 | Srivastava |
| 5,328,688 A | 7/1994 | Roizman |
| 5,403,484 A | 4/1995 | Ladner et al. |
| 5,474,935 A | 12/1995 | Chatterjee et al. |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,585,362 A | 12/1996 | Wilson et al. |
| 5,622,856 A | 4/1997 | Natsoulis |
| 5,631,237 A | 5/1997 | Dzau et al. |
| 5,639,641 A | 6/1997 | Pedersen et al. |
| 5,658,776 A | 8/1997 | Flotte et al. |
| 5,661,033 A | 8/1997 | Ho et al. |
| 5,670,488 A | 9/1997 | Gregory et al. |
| 5,693,509 A | 12/1997 | Cotten et al. |
| 5,693,761 A | 12/1997 | Queen et al. |

(Continued)

FOREIGN PATENT DOCUMENTS

| | | |
|---|---|---|
| CN | 107043752 A | 8/2017 |
| EP | 0088046 A2 | 9/1983 |

(Continued)

OTHER PUBLICATIONS

Arranz et al., The impact of stress on tumor growth: peripheral CRF mediates tumor-promoting effects of stress, Molecular Cancer, (9)1:261 (2010).

Castro et al., The use of inclusion bodies, isolated from *Escherichia coli* expressing corticotrophin-releasing hormone precursor, to raise specific antibodies against the neuropeptide moiety, Journal of Molecular Endocrinology, 5(3):221-230 (1990).

(Continued)

*Primary Examiner* — Olga N Chernyshev
(74) *Attorney, Agent, or Firm* — MARSHALL, GERSTEIN & BORUN LLP

(57) ABSTRACT

Disclosed herein are materials and methods for the treatment of stress-related disorders and cancer. The disclosure provides an antibody, or antigen binding fragment thereof, that specifically binds to a region of corticotropin-releasing hormone (CRH). The disclosure also provides methods of treating a disorder associated with HPA axis activation, such as a stress-related disorder or cancer, comprising administering to a subject in need thereof an antibody or antigen binding fragment thereof described herein in an amount effective to treat the disorder.

8 Claims, 22 Drawing Sheets

Specification includes a Sequence Listing.

(56) References Cited

U.S. PATENT DOCUMENTS

| | | | |
|---|---|---|---|
| 5,693,762 | A | 12/1997 | Queen et al. |
| 5,702,892 | A | 12/1997 | Mulligan-Kehoe |
| 5,707,618 | A | 1/1998 | Armentano et al. |
| 5,714,352 | A | 2/1998 | Jakobobits et al. |
| 5,733,790 | A | 3/1998 | Potter et al. |
| 5,773,289 | A | 6/1998 | Samulski et al. |
| 5,780,279 | A | 7/1998 | Matthews et al. |
| 5,789,390 | A | 8/1998 | Descamps et al. |
| 5,792,453 | A | 8/1998 | Hammond et al. |
| 5,821,047 | A | 10/1998 | Garrard et al. |
| 5,824,520 | A | 10/1998 | Mulligan-Kehoe |
| 5,824,544 | A | 10/1998 | Armentano et al. |
| 5,830,727 | A | 11/1998 | Wang et al. |
| 5,834,441 | A | 11/1998 | Philip et al. |
| 5,837,500 | A | 11/1998 | Ladner et al. |
| 5,849,571 | A | 12/1998 | Glorioso et al. |
| 5,851,521 | A | 12/1998 | Branellec et al. |
| 5,855,885 | A | 1/1999 | Smith et al. |
| 5,856,152 | A | 1/1999 | Wilson et al. |
| 5,858,657 | A | 1/1999 | Winter et al. |
| 5,863,541 | A | 1/1999 | Samulski et al. |
| 5,871,907 | A | 2/1999 | Winter et al. |
| 5,879,934 | A | 3/1999 | Deluca |
| 5,969,108 | A | 10/1999 | Mccafferty et al. |
| 6,020,305 | A | 2/2000 | Theoharides |
| 6,057,098 | A | 5/2000 | Buechler et al. |
| 6,225,447 | B1 | 5/2001 | Winter et al. |
| 6,265,150 | B1 | 7/2001 | Terstappen et al. |
| 2002/0197266 | A1 | 12/2002 | Debinski |

FOREIGN PATENT DOCUMENTS

| | | |
|---|---|---|
| EP | 0133988 A2 | 3/1985 |
| EP | 0058481 B1 | 10/1986 |
| EP | 0143949 B1 | 10/1988 |
| EP | 0036676 B2 | 9/1990 |
| EP | 0239400 B1 | 8/1994 |
| EP | 1094072 A1 | 4/2001 |
| GB | 2188638 A | 10/1987 |
| WO | 93/15722 A1 | 8/1993 |

OTHER PUBLICATIONS

Futch et al., An anti-CRF antibody suppresses the HPA axis and reverses stress-induced phenotypes, Journal of Experimental Medicine, 216(11):2479-2491 (2019).

Hagan et al., Development of a two-site immunoradiometric assay for rat/human corticotrophin-releasing factor—Application to the measurement of interleukin-1ß-stimulated production of hypothalamic CRF in vitro, Journal of Immunological Methods, 160(1):11-18 (1993).

Linton et al., Corticotrophin-releasing hormone (CRH)-binding protein interference with CRH antibody binding: implications for direct CRH immunoassay, Journal of Endocrinology, 146(1):45-53 (1995).

Androulidaki et al., Corticotropin Releasing Factor promotes breast cancer cell motility and invasiveness, Mol. Cancer, 8:30 (2009).

Chothia et al., Canonical structures for the hypervariable regions of immunoglobulins, J. Mol. Biol., 196:901-917 (1987).

Chothia et al., Conformations of immunoglobulin hypervariable regions, Nature, 342:877-883 (1989).

Cote et al., Generation of human monoclonal antibodies reactive with cellular antigens, Proc. Natl. Acad. Sci. USA, 80(7):2026-2030 (1983).

Eppstein et al., Biological activity of liposome-encapsulated murine interferon gamma is mediated by a cell membrane receptor, Proc. Natl. Acad. Sci. USA, 82(11):3688-3692 (1985).

Hu et al., Minibody: A novel engineered anti-carcinoembryonic antigen antibody fragment (single-chain Fv-CH3) which exhibits rapid, high-level targeting of xenografts, Cancer Res., 56(13):3055-3061 (1996).

International Application No. PCT/US19/36337, International Preliminary Report on Patentability, mailed Dec. 24, 2020.

International Application No. PCT/US19/36337, International Search Report and Written Opinion, mailed Oct. 2, 2019.

Karpovsky et al., Production of target-specific effector cells using hetero-cross-linked aggregates containing anti-target cell and anti-Fc gamma receptor antibodies, J. Exp. Med., 160(6):1686-701 (1984).

Kim et al., Minimal requirement for a lentivirus vector based on human immunodeficiency virus type 1, J. Virol., 72(1):811-816 (1998).

Kohler et al., Continuous cultures of fused cells secreting antibody of predefined specificity, Nature, 256:495-497 (1975).

Kortt et al., Dimeric and trimeric antibodies: high avidity scFvs for cancer targeting, Biomol Eng., 18(3):95-108 (2001).

Monison et al., Chimeric human antibody molecules: mouse antigen-binding domains with human constant region domains, Proc. Natl. Acad. Sci. USA, 81(21):6851-6855 (1984).

Orlandi et al., Cloning immunoglobulin variable domains for expression by the polymerase chain reaction, Proc. Natl. Acad. Sci. USA, 86(10):3833-3837 (1989).

Perricaudet et al., Widespread long-term gene transfer to mouse skeletal muscles and heart, J. Clin. Invest., 90:626-630 (1992).

Philips et al., Therapeutic uses of anti-PD-1 and anti-PD-L1 antibodies, Int. Immunol., 27(1):39-46 (2015).

Quantin et al., Adenovirus as an expression vector in muscle cells in vivo, Proc. Natl. Acad. Sci. USA, 89(7):2581-2584 (1992).

Raadsheer et al., Corticotropin-releasing hormone mRNA levels in the paraventricular nucleus of patients with Alzheimer's disease and depression, Am. J. Psychiatry, 152(9):1372-6 (1995).

Reiter et al., Engineering interchain disulfide bonds into conserved framework regions of Fv fragments: improved biochemical characteristics of recombinant immunotoxins containing disulfide-stabilized Fv, Protein Engineering, 7(5):697-704 (1994).

Structural Genomics Consortium, Protein production and purification, Nat Methods, 5(2):135-146 (2008).

Todorovska et al., Design and application of diabodies, triabodies and tetrabodies for cancer targeting, J. Immunol. Methods, 248:47-66 (2001).

Winter et al., Man-made antibodies, Nature, 349:293-299 (1991).

WT mice were injected subcutaneously with 200ug of CRH-Vaccine peptide emulsified in 200uL of Complete Freund's Adjuvant. This is followed by two boosts of 200ug of vaccine peptide emulsified in Incomplete Freund's Adjuvant injected IP at two week intervals. Following the final boost serum was collected and assayed for Anti-CRH titers via direct ELISA.

Antibody B
Kd=<10E-12

Antibody A
Kd=10E-8 n=9 groups of WT mice were injected IP with 25 mg/kg of either Anti-CRH antibody or saline 12 hours before being exposed to 30 minutes of restraint stress. Plasma was drawn at four time points and assayed for corticosterone levels via radioimmunoassay.

n=10 groups of WT mice identical experiment

WT mouse injected intracerebroventricularly with AAV8-CRH overexpresses CRH within the brain and develops cushingoid phenotype. Hair loss, red skin, and obesity. One injection of Antibody B antibody is able to reverse hair loss.

Figure 5

Antibody A: Kd=2.09E-8

Vaccine Used

KLH-SEEPPISLDLTFHLL  SEQ ID NO: 2

Heavy Chain

METDTLLLWVLLLWVPGSTGDGVQCEVK
LVESGGGLVKPGGSLKLSCAASGFTFSSY
AMSWVRQTPEKRLEWVASISIGGSTYYR
DSVKGRCTISRDNAKNILYLQMRSLRSED
TAMYYCARRGMDYWGQGTSVTVSS
SEQ ID NO:11

Light Chain

DIVITQDELSNPVTSGESVSISCRSSKSLL
YKDGKTYLNWFLQRPGQSPQLLIYLMST
RASGVSDRFSGSGSGTDFTLEISRVKAE
DVGVYYCQQLVEYPLTFGAGTKLELKRAS
GHHHHHGSDYKDDDDK
SEQ ID NO: 10

Antibody B: Kd=<1.0E-12

Vaccine Used

OVA-SEEPPISLDLTFHLLREVLEM  SEQ ID NO: 3

Heavy Chain

EVQLQQSGPELVKPGVSMKISCKASGYSFT
DSTMNWVKQSHGKNLEWIGLIHPDNGGTIY
NQKFKGKATLTVHKSSSTAYMELLSLTSEDSA
VYYCANGFAYWGQGTLVTVSAAKTTPPSVY
SEQ ID NO: 19
PLAPGSAA

Light Chain

DVVMTQTPLSLPVSLGDQASISCRSSQSLLH
SNGNTYLHWYLQKPGQSPELLIYKVSNRFS
GVPDRFSGSGSGTDFTLKISRVEAEDLGVYF
CSQSTHVPLTFGAGTKLELK  SEQ ID NO: 18

Figure 6

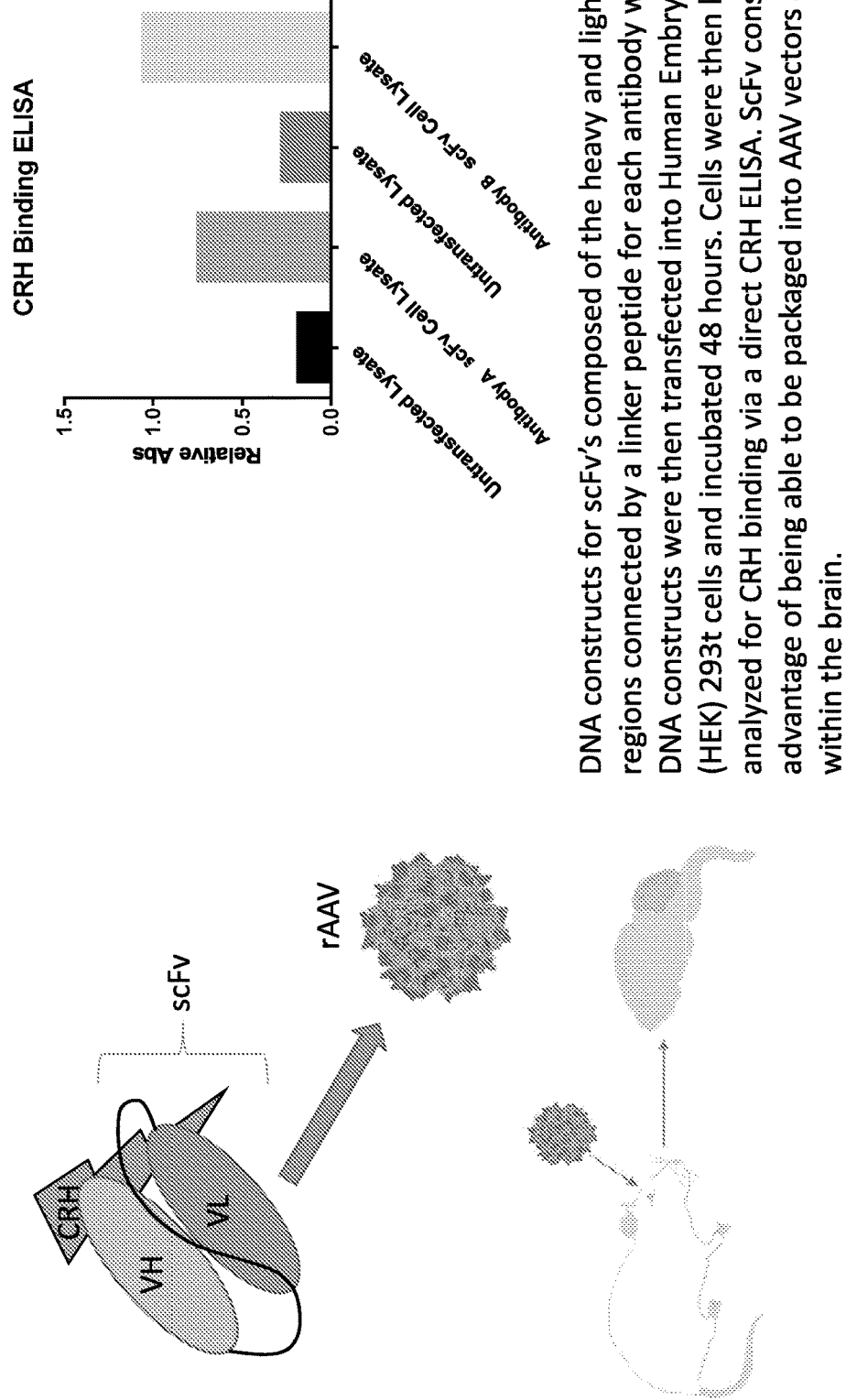

DNA constructs for scFv's composed of the heavy and light variable regions connected by a linker peptide for each antibody were generated. DNA constructs were then transfected into Human Embryonic Kidney (HEK) 293t cells and incubated 48 hours. Cells were then lysed and analyzed for CRH binding via a direct CRH ELISA. ScFv constructs offer the advantage of being able to be packaged into AAV vectors and transduced within the brain.

Figure 7

Several strategies for humanization of our mouse antibodies exist. Below for example is a comparison between the variable region of Antibody B and the most similar human variable framework. Highlighted are the complementarity determining regions (CDR's) of our antibody. We will be able to alter the framework of our variable regions to match those of the human framework without altering the Antibody B CDR's. Providing a humanized Anti-CRH construct that would be checked for retained affinity and then moved into human trials.

```
Score            Expect    Method                              Identities       Positives      Gaps
197 bits(500)    3e-65     Compositional matrix adjust.        100/131(76%)     108/131(82%)   5/131(3%)

Query  1    EVQLQQSGPELVKPGVSMKISCKASGYSFTDSTMNWVKQSHGKNLEWIGLIHPDNGGTIY    60
            EVQLQQ G ELVKPG S+KISCKASGY FTD M+WVKQSHGK+LEWIG I P+  + Y
Sbjct  20   EVQLQQFGAELVKPGTSVKISCKASGYIFTDYNMDWVKQSHGKSLEWIGDIDPNFDSSSY    79

Query  61   NQKFKGKATLTVHKSSSTAYMELLSLTSEDSAVYYCAN------GFAYWGQGTLVTVSAAK   115
            NQKFKGKATLTV KSS+TAYMEL SLTSED+AVYYCA      G  YWGQGT VTVS+AK
Sbjct  80   NQKFKGKATLTVDKSSNTAYMELRSLTSEDTAVYYCARGGFPYGMDYWGQGTSVTVSSAK   139

Query  116  TTPPSVYPLAP   126
            TTPPSVYPLAP
Sbjct  140  TTPPSVYPLAP   150
```

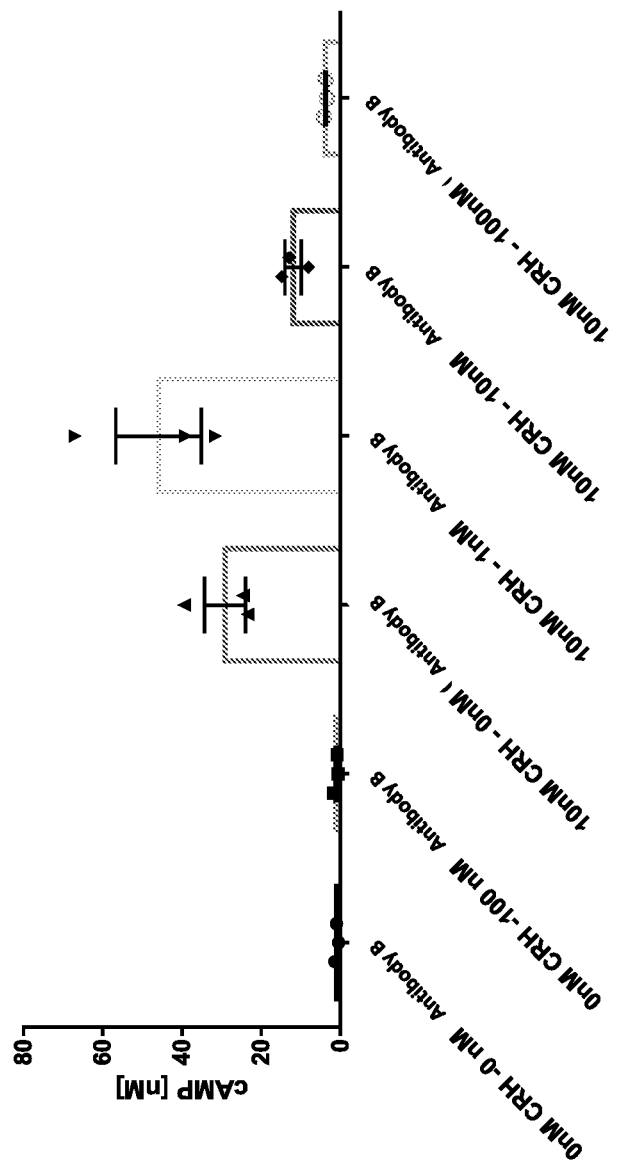

Figure 9
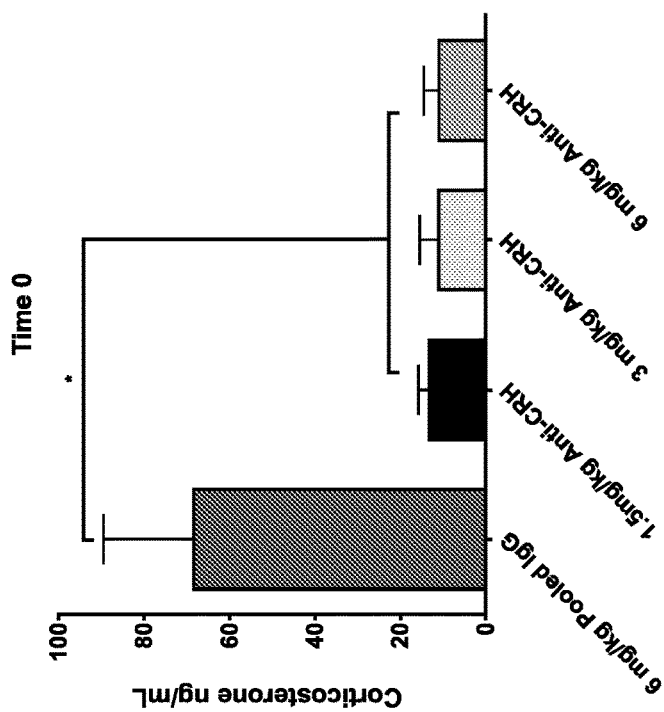
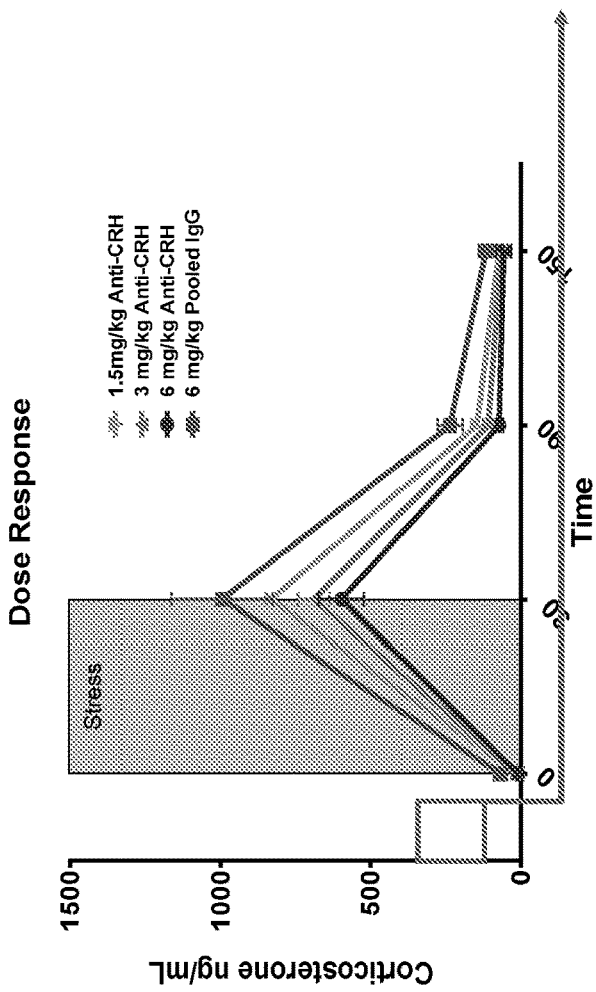

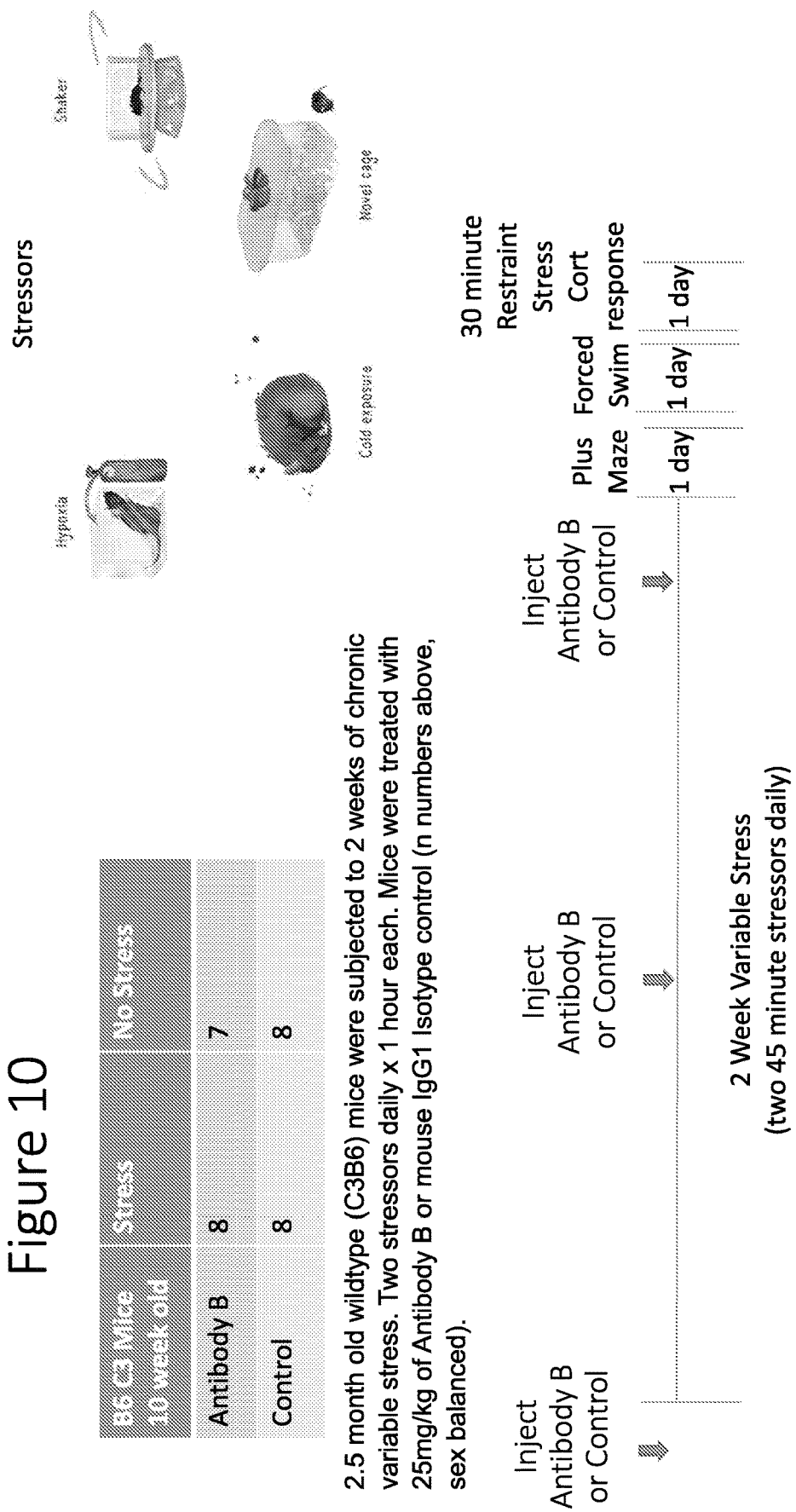

Mesenteric Fat weight/Body Weight

Subcutaneous Fat weight/Body Weight

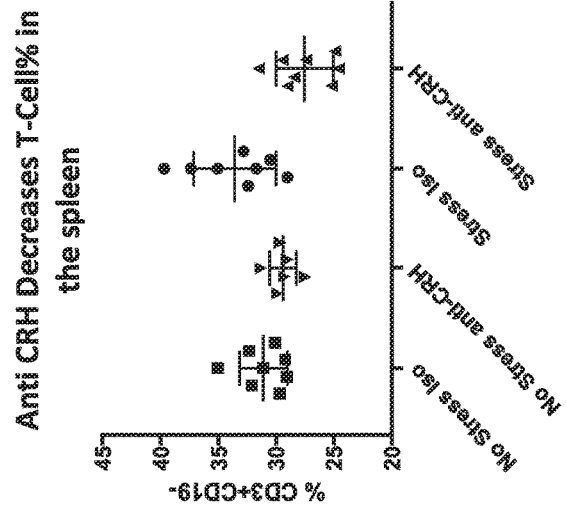
Figure 11E
Figure 11F
Figure 11G
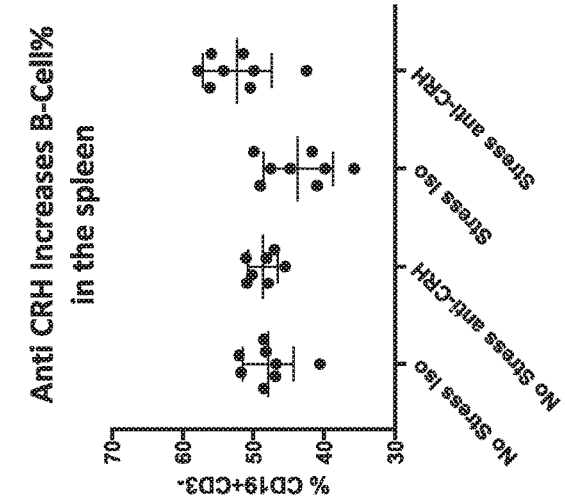
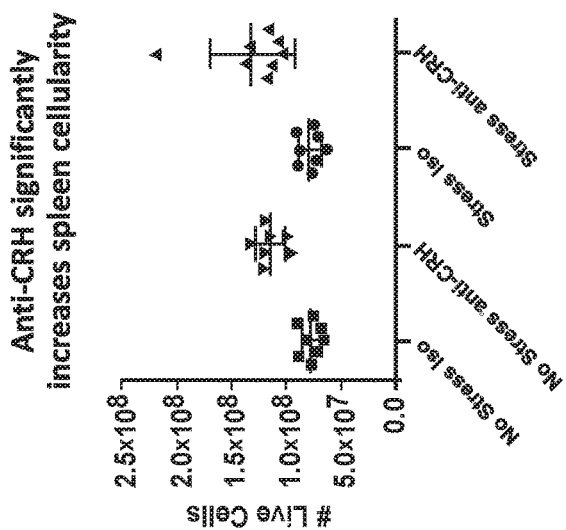
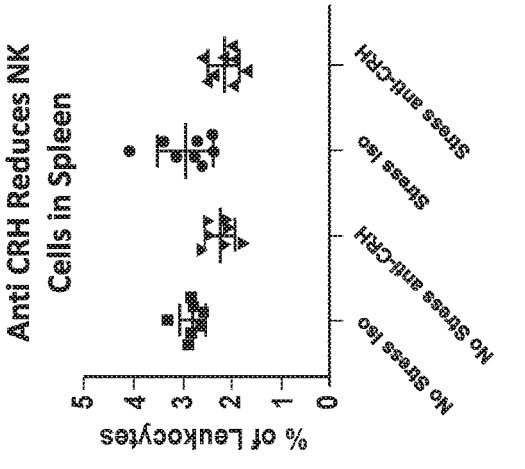
Figure 11H
Figure 11I
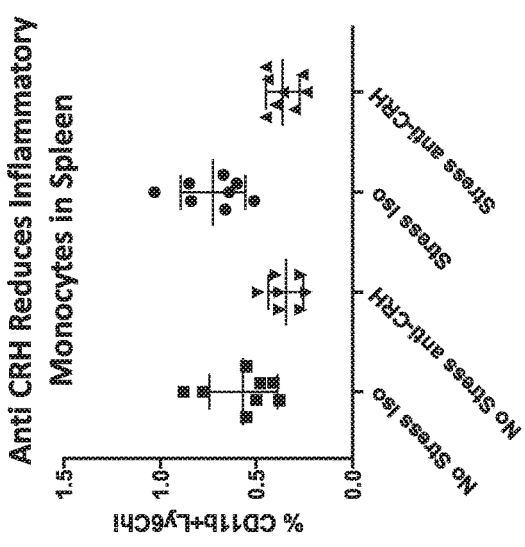

Figure 13F
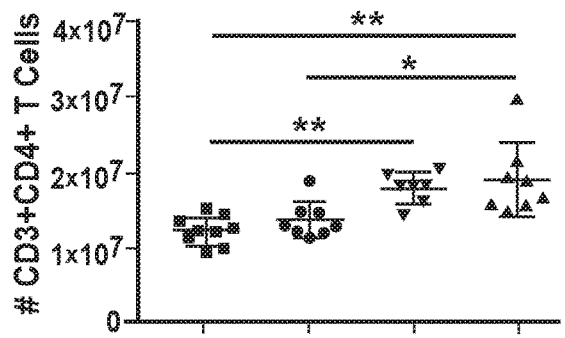
Figure 13G
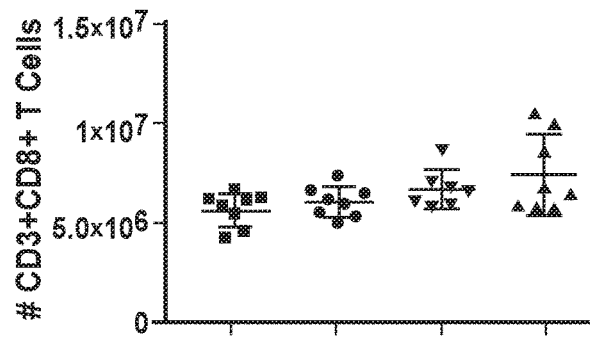
Figure 13H
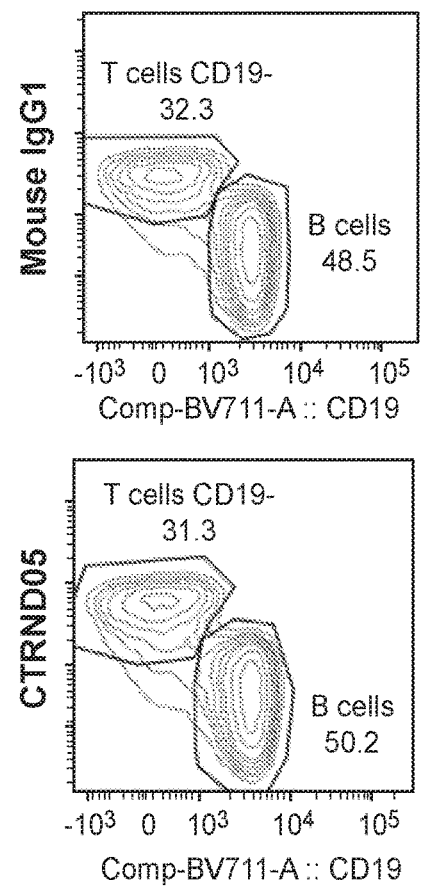
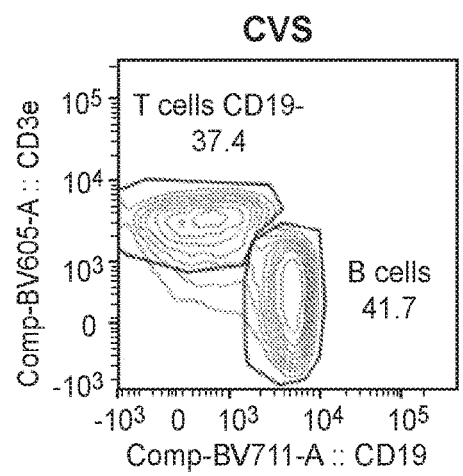
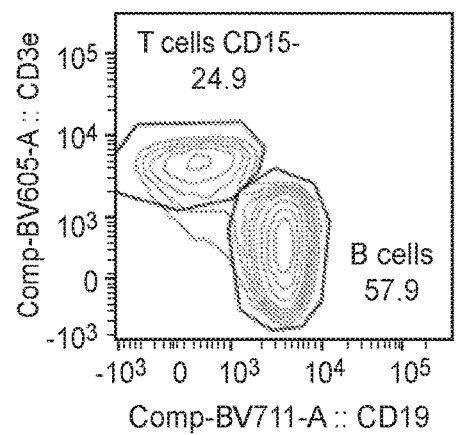

Figure 13I
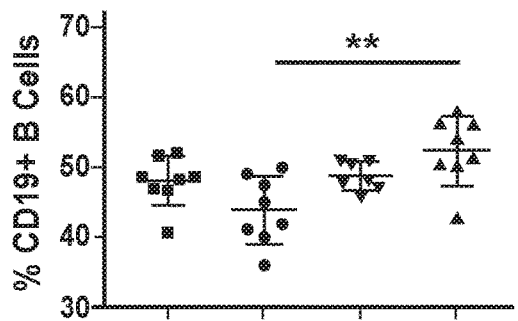
Figure 13J
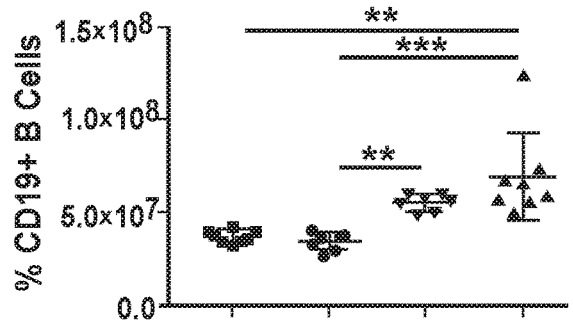
Figure 13K
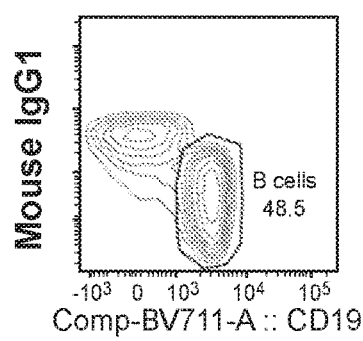
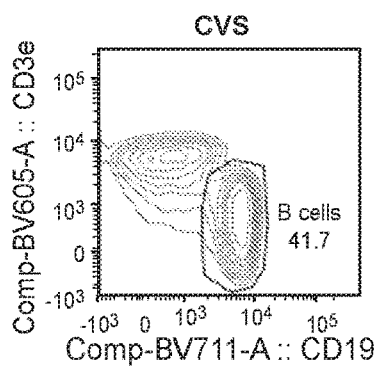
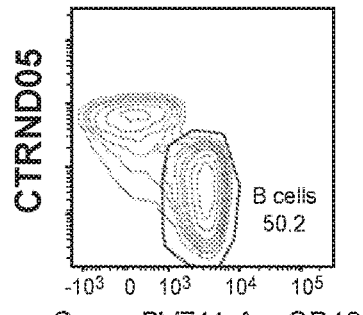
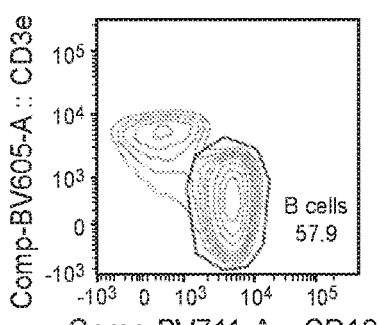
Figure 13L
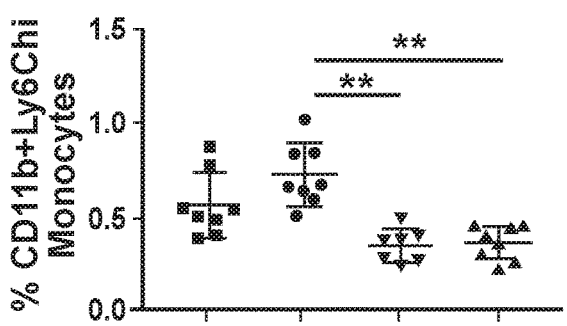
Figure 13M
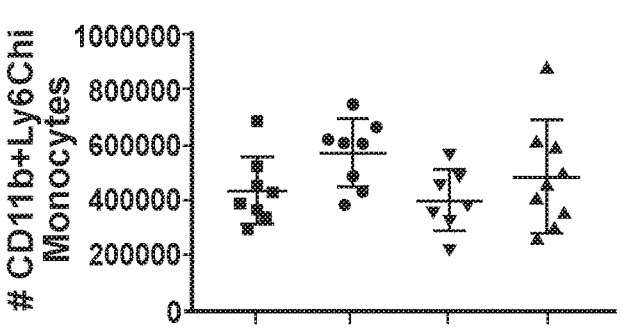

BLI determined binding affinity of CRF peptide and Antibody B

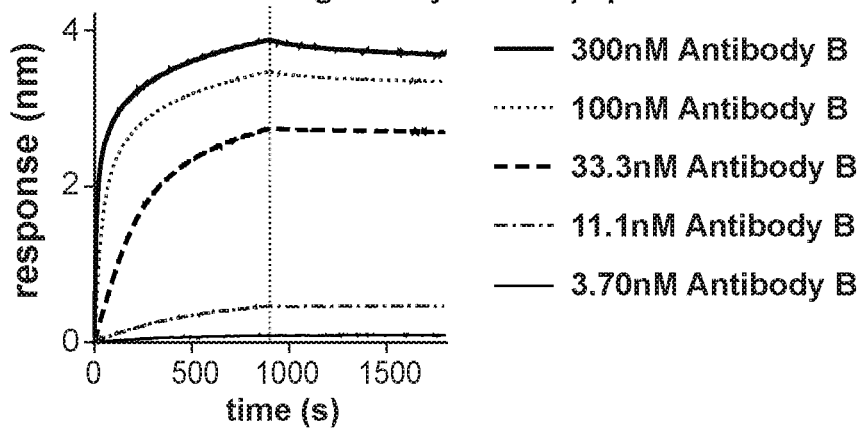

| Sample ID | Response | KD(M) | kon(1/Ms) | kdis(1/s) | Full R^2 |
|---|---|---|---|---|---|
| 300nM Antibody B | 3.8813 | <1.0E-12 | 9.75E+04 | <1.0E-07 | 0.9959 |
| 100nM Antibody B | 3.4724 | <1.0E-12 | 9.75E+04 | <1.0E-07 | 0.9959 |
| 33.3nM Antibody B | 2.7419 | <1.0E-12 | 9.75E+04 | <1.0E-07 | 0.9959 |
| 11.1nM Antibody B | 0.4675 | <1.0E-12 | 9.75E+04 | <1.0E-07 | 0.9959 |
| 3.70nM Antibody B | 0.0887 | <1.0E-12 | 9.75E+04 | <1.0E-07 | 0.9959 |
| 1.23nM Antibody B | 0.0154 | <1.0E-12 | 9.75E+04 | <1.0E-07 | 0.9959 |
| 0.412nM Antibody B | 0.0087 | <1.0E-12 | 9.75E+04 | <1.0E-07 | 0.9959 |

BLI determined binding affinity of UNCII peptide and Antibody B

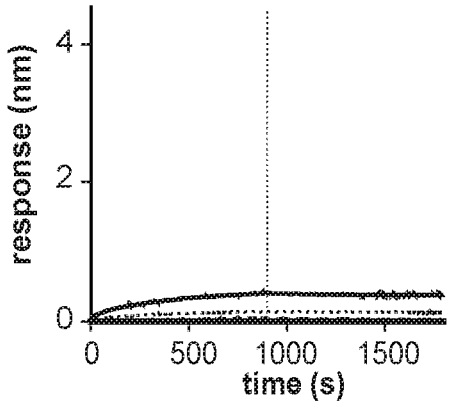

| Sample ID | Response | KD(M) | kon(1/Ms) | kdis(1/s) | Full R^2 |
|---|---|---|---|---|---|
| 300nM Antibody B | 0.3625 | 4.24E-09 | 1.40E+04 | 5.93E-05 | 0.9944 |
| 100nM Antibody B | 0.1315 | 4.24E-09 | 1.40E+04 | 5.93E-05 | 0.9944 |
| 33.3nM Antibody B | 0.0486 | 4.24E-09 | 1.40E+04 | 5.93E-05 | 0.9944 |
| 11.1nM Antibody B | 0.0253 | 4.24E-09 | 1.40E+04 | 5.93E-05 | 0.9944 |
| 3.70nM Antibody B | 0.0122 | 4.24E-09 | 1.40E+04 | 5.93E-05 | 0.9944 |
| 1.23nM Antibody B | 0.0144 | 4.24E-09 | 1.40E+04 | 5.93E-05 | 0.9944 |
| 0.412nM Antibody B | 0.0049 | 4.24E-09 | 1.40E+04 | 5.93E-05 | 0.9944 |

Figure 16

SEQUENCE LISTING

<160> NUMBER OF SEQ ID NOS: 24

<210> SEQ ID NO 1
<211> LENGTH: 41
<212> TYPE: PRT
<213> ORGANISM: Homo sapiens
<220> FEATURE:
<221> NAME/KEY: MISC_FEATURE
<223> OTHER INFORMATION: CRH Human

<400> SEQUENCE: 1

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 2
<211> LENGTH: 15
<212> TYPE: PRT
<213> ORGANISM: Homo sapiens
<220> FEATURE:
<221> NAME/KEY: MISC_FEATURE
<223> OTHER INFORMATION: amino acids 1-15 of SEQ ID NO: 1

<400> SEQUENCE: 2

Ser Glu Glu Pro Pro Ile Ser Leu Asp Leu Thr Phe His Leu Leu
1               5                   10                  15

<210> SEQ ID NO 3
<211> LENGTH: 21
<212> TYPE: PRT
<213> ORGANISM: Homo sapiens
<220> FEATURE:
<221> NAME/KEY: MISC_FEATURE
<223> OTHER INFORMATION: amino acids 1-21 of SEQ ID NO: 1

<400> SEQUENCE: 3

Ser Glu Glu Pro Pro Ile Ser Leu Asp Leu Thr Phe His Leu Leu Arg
1               5                   10                  15

Glu Val Leu Glu Met
            20

<210> SEQ ID NO 4
<211> LENGTH: 8
<212> TYPE: PRT
<213> ORGANISM: Mus musculus
<220> FEATURE:
<221> NAME/KEY: MISC_FEATURE
<223> OTHER INFORMATION: Antibody A HCDR1

<400> SEQUENCE: 4

Gly Phe Thr Phe Ser Ser Tyr Ala
1               5

<210> SEQ ID NO 5
<211> LENGTH: 7
<212> TYPE: PRT
<213> ORGANISM: Mus musculus
<220> FEATURE:
<221> NAME/KEY: MISC_FEATURE
<223> OTHER INFORMATION: Antibody A HCDR2

<400> SEQUENCE: 5

Ile Ser Ile Gly Gly Ser Thr

-continued

```
<210> SEQ ID NO 6
<211> LENGTH: 8
<212> TYPE: PRT
<213> ORGANISM: Mus musculus
<220> FEATURE:
<221> NAME/KEY: MISC_FEATURE
<223> OTHER INFORMATION: Antibody A HCDR3

<400> SEQUENCE: 6

Cys Ala Arg Arg Gly Met Asp Tyr
1               5

<210> SEQ ID NO 7
<211> LENGTH: 16
<212> TYPE: PRT
<213> ORGANISM: Mus musculus
<220> FEATURE:
<221> NAME/KEY: MISC_FEATURE
<223> OTHER INFORMATION: Antibody A LCDR1

<400> SEQUENCE: 7

Arg Ser Ser Lys Ser Leu Leu Tyr Lys Asp Gly Lys Thr Tyr Leu Asn
1               5                   10                  15

<210> SEQ ID NO 8
<211> LENGTH: 6
<212> TYPE: PRT
<213> ORGANISM: Mus musculus
<220> FEATURE:
<221> NAME/KEY: MISC_FEATURE
<223> OTHER INFORMATION: Antibody A LCDR2

<400> SEQUENCE: 8

Leu Met Ser Thr Arg Ala
1               5

<210> SEQ ID NO 9
<211> LENGTH: 13
<212> TYPE: PRT
<213> ORGANISM: Mus musculus
<220> FEATURE:
<221> NAME/KEY: MISC_FEATURE
<223> OTHER INFORMATION: Antibody A LCDR3

<400> SEQUENCE: 9

Gln Leu Val Glu Tyr Pro Leu Thr Phe Gly Ala Gly Thr
1               5                   10

<210> SEQ ID NO 10
<211> LENGTH: 132
<212> TYPE: PRT
<213> ORGANISM: Mus musculus
<220> FEATURE:
<221> NAME/KEY: MISC_FEATURE
<223> OTHER INFORMATION: Antibody A VL

<400> SEQUENCE: 10

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
            35                  40                  45

Pro Gln Leu Leu Ile Tyr Leu Met Ser Thr Arg Ala Ser Gly Val Ser
```

```
                50                  55                  60
Asp Arg Phe Ser Gly Ser Gly Thr Asp Phe Thr Leu Glu Ile
 65                  70                  75                  80

Ser Arg Val Lys Ala Glu Asp Val Gly Val Tyr Tyr Cys Gln Gln Leu
                 85                  90                  95

Val Glu Tyr Pro Leu Thr Phe Gly Ala Gly Thr Lys Leu Glu Leu Lys
            100                 105                 110

Arg Ala Ser Gly His His His His His Gly Ser Asp Tyr Lys Asp
        115                 120                 125

Asp Asp Asp Lys
    130

<210> SEQ ID NO 11
<211> LENGTH: 138
<212> TYPE: PRT
<213> ORGANISM: Mus musculus
<220> FEATURE:
<221> NAME/KEY: MISC_FEATURE
<223> OTHER INFORMATION: Antibody A VH

<400> SEQUENCE: 11

Met Glu Thr Asp Thr Leu Leu Leu Trp Val Leu Leu Trp Val Pro
  1               5                  10                  15

Gly Ser Thr Gly Asp Gly Val Gln Cys Glu Val Lys Leu Val Glu Ser
                 20                  25                  30

Gly Gly Gly Leu Val Lys Pro Gly Gly Ser Leu Lys Leu Ser Cys Ala
             35                  40                  45

Ala Ser Gly Phe Thr Phe Ser Ser Tyr Ala Met Ser Trp Val Arg Gln
         50                  55                  60

Thr Pro Glu Lys Arg Leu Glu Trp Val Ala Ser Ile Ser Ile Gly Gly
 65                  70                  75                  80

Ser Thr Tyr Tyr Arg Asp Ser Val Lys Gly Arg Cys Thr Ile Ser Arg
                 85                  90                  95

Asp Asn Ala Lys Asn Ile Leu Tyr Leu Gln Met Arg Ser Leu Arg Ser
            100                 105                 110

Glu Asp Thr Ala Met Tyr Tyr Cys Ala Arg Arg Gly Met Asp Tyr Trp
        115                 120                 125

Gly Gln Gly Thr Ser Val Thr Val Ser Ser
    130                 135

<210> SEQ ID NO 12
<211> LENGTH: 8
<212> TYPE: PRT
<213> ORGANISM: Mus musculus
<220> FEATURE:
<221> NAME/KEY: MISC_FEATURE
<223> OTHER INFORMATION: Antibody B HCDR1

<400> SEQUENCE: 12

Gly Tyr Ser Phe Thr Asp Ser Thr
  1               5

<210> SEQ ID NO 13
<211> LENGTH: 8
<212> TYPE: PRT
<213> ORGANISM: Mus musculus
<220> FEATURE:
<221> NAME/KEY: MISC_FEATURE
<223> OTHER INFORMATION: Antibody B HCDR2

<400> SEQUENCE: 13
```

```
Ile His Pro Asp Asn Gly Gly Thr
1               5

<210> SEQ ID NO 14
<211> LENGTH: 6
<212> TYPE: PRT
<213> ORGANISM: Mus musculus
<220> FEATURE:
<221> NAME/KEY: MISC_FEATURE
<223> OTHER INFORMATION: Antibody B HCDR3

<400> SEQUENCE: 14

Ala Asn Gly Phe Ala Tyr
1               5

<210> SEQ ID NO 15
<211> LENGTH: 11
<212> TYPE: PRT
<213> ORGANISM: Mus musculus
<220> FEATURE:
<221> NAME/KEY: MISC_FEATURE
<223> OTHER INFORMATION: Antibody B LCDR1

<400> SEQUENCE: 15

Gln Ser Leu Leu His Ser Asn Gly Asn Thr Tyr
1               5                   10

<210> SEQ ID NO 16
<211> LENGTH: 3
<212> TYPE: PRT
<213> ORGANISM: Mus musculus
<220> FEATURE:
<221> NAME/KEY: MISC_FEATURE
<223> OTHER INFORMATION: Antibody B LCDR2

<400> SEQUENCE: 16

Lys Val Ser
1

<210> SEQ ID NO 17
<211> LENGTH: 9
<212> TYPE: PRT
<213> ORGANISM: Mus musculus
<220> FEATURE:
<221> NAME/KEY: MISC_FEATURE
<223> OTHER INFORMATION: Antibody B LCDR3

<400> SEQUENCE: 17

Ser Gln Ser Thr His Val Pro Leu Thr
1               5

<210> SEQ ID NO 18
<211> LENGTH: 112
<212> TYPE: PRT
<213> ORGANISM: Mus musculus
<220> FEATURE:
<221> NAME/KEY: MISC_FEATURE
<223> OTHER INFORMATION: Antibody B VL

<400> SEQUENCE: 18

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45
```

```
Pro Glu Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Leu Lys
            100                 105                 110

<210> SEQ ID NO 19
<211> LENGTH: 130
<212> TYPE: PRT
<213> ORGANISM: Mus musculus
<220> FEATURE:
<221> NAME/KEY: MISC_FEATURE
<223> OTHER INFORMATION: Antibody B VH

<400> SEQUENCE: 19

Glu Val Gln Leu Gln Gln Ser Gly Pro Glu Leu Val Lys Pro Gly Val
 1               5                  10                  15

Ser Met Lys Ile Ser Cys Lys Ala Ser Gly Tyr Ser Phe Thr Asp Ser
             20                  25                  30

Thr Met Asn Trp Val Lys Gln Ser His Gly Lys Asn Leu Glu Trp Ile
         35                  40                  45

Gly Leu Ile His Pro Asp Asn Gly Gly Thr Ile Tyr Asn Gln Lys Phe
     50                  55                  60

Lys Gly Lys Ala Thr Leu Thr Val His Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Asn Gly Phe Ala Tyr Trp Gly Gln Gly Thr Leu Val Thr Val Ser
            100                 105                 110

Ala Ala Lys Thr Thr Pro Pro Ser Val Tyr Pro Leu Ala Pro Gly Ser
        115                 120                 125

Ala Ala
    130

<210> SEQ ID NO 20
<211> LENGTH: 336
<212> TYPE: DNA
<213> ORGANISM: Mus musculus
<220> FEATURE:
<221> NAME/KEY: misc_feature
<223> OTHER INFORMATION: Antibody B VL

<400> SEQUENCE: 20
gatgtggtga tgacccagac cccgctgagc ctgccggtga gcctgggcga tcaggcgagc      60
attagctgcc gcagcagcca gagcctgctg catagcaacg gcaacaccta tctgcattgg     120
tatctgcaga aaccgggcca gagcccggaa ctgctgattt ataaagtgag caaccgcttt     180
agcggcgtgc cggatcgctt tagcggcagc ggcagcggca ccgatttttac cctgaaaatt     240 agccgcgtgg aagcggaaga tctgggcgtg tattttttgca gccagagcac ccatgtgccg     300
ctgacctttg gcgcgggcac caaactggaa ctgaaa                                336

<210> SEQ ID NO 21
<211> LENGTH: 342
<212> TYPE: DNA
<213> ORGANISM: Mus musculus
```

<220> FEATURE:
<221> NAME/KEY: misc_feature
<223> OTHER INFORMATION: Antibody B VH

<400> SEQUENCE: 21

```
gaagtccagc tccagcagag tggtcccgaa ctggttaagc cgggagtgtc tatgaagatt        60
agctgtaagg catccggtta ctcttttaca gactctacga tgaattgggt caaacaatcc       120
cacgggaaga acttggagtg gataggtctg atccaccctg ataacggcgg aacgatctac       180
aaccagaagt ttaaagggaa agcaaccctg actgtacaca agtcttcatc tactgcgtac       240
atggagttgc tcagccttac ctccgaggat agtgcagttt actactgtgc taacggtttc       300
gcatactggg ggcaaggaac gctcgtgacg gtttcagccg cg                          342
```

<210> SEQ ID NO 22
<211> LENGTH: 285
<212> TYPE: PRT
<213> ORGANISM: Mus musculus
<220> FEATURE:
<221> NAME/KEY: MISC_FEATURE
<223> OTHER INFORMATION: Antibody A ScFV

<400> SEQUENCE: 22

```
Met Glu Thr Asp Thr Leu Leu Leu Trp Val Leu Leu Leu Trp Val Pro
1               5                   10                  15

Gly Ser Thr Gly Asp Gly Val Gln Cys Glu Val Lys Leu Val Glu Ser
            20                  25                  30

Gly Gly Gly Leu Val Lys Pro Gly Gly Ser Leu Lys Leu Ser Cys Ala
        35                  40                  45

Ala Ser Gly Phe Thr Phe Ser Ser Tyr Ala Met Ser Trp Val Arg Gln
    50                  55                  60

Thr Pro Glu Lys Arg Leu Glu Trp Val Ala Ser Ile Ser Ile Gly Gly
65                  70                  75                  80

Ser Thr Tyr Tyr Arg Asp Ser Val Lys Gly Arg Cys Thr Ile Ser Arg
                85                  90                  95

Asp Asn Ala Lys Asn Ile Leu Tyr Leu Gln Met Arg Ser Leu Arg Ser
            100                 105                 110

Glu Asp Thr Ala Met Tyr Tyr Cys Ala Arg Arg Gly Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Ser Asp Ile Val Ile Thr Gln Asp
145                 150                 155                 160

Glu Leu Ser Asn Pro Val Thr Ser Gly Glu Ser Val Ser Ile Ser Cys
                165                 170                 175

Arg Ser Ser Lys Ser Leu Leu Tyr Lys Asp Gly Lys Thr Tyr Leu Asn
            180                 185                 190

Trp Phe Leu Gln Arg Pro Gly Gln Ser Pro Gln Leu Leu Ile Tyr Leu
        195                 200                 205

Met Ser Thr Arg Ala Ser Gly Val Ser Asp Arg Phe Ser Gly Ser Gly
    210                 215                 220

Ser Gly Thr Asp Phe Thr Leu Glu Ile Ser Arg Val Lys Ala Glu Asp
225                 230                 235                 240

Val Gly Val Tyr Tyr Cys Gln Gln Leu Val Glu Tyr Pro Leu Thr Phe
                245                 250                 255

Gly Ala Gly Thr Lys Leu Glu Leu Lys Arg Ala Ser Gly His His His
            260                 265                 270
```

```
His His His Gly Ser Asp Tyr Lys Asp Asp Asp Lys
        275                 280                 285

<210> SEQ ID NO 23
<211> LENGTH: 296
<212> TYPE: PRT
<213> ORGANISM: Mus musculus
<220> FEATURE:
<221> NAME/KEY: MISC_FEATURE
<223> OTHER INFORMATION: Antibody B ScFv

<400> SEQUENCE: 23

Met Glu Thr Asp Thr Leu Leu Leu Trp Val Leu Leu Leu Trp Val Pro
1               5                   10                  15

Gly Ser Thr Gly Asp Glu Val Gln Leu Gln Gln Ser Gly Pro Glu Leu
            20                  25                  30

Val Lys Pro Gly Val Ser Met Lys Ile Ser Cys Lys Ala Ser Gly Tyr
        35                  40                  45

Ser Phe Thr Asp Ser Thr Met Asn Trp Val Lys Gln Ser His Gly Lys
    50                  55                  60

Asn Leu Glu Trp Ile Gly Leu Ile His Pro Asp Asn Gly Gly Thr Ile
65                  70                  75                  80

Tyr Asn Gln Lys Phe Lys Gly Lys Ala Thr Leu Thr Val His Lys Ser
                85                  90                  95

Ser Ser Thr Ala Tyr Met Glu Leu Leu Ser Leu Thr Ser Glu Asp Ser
            100                 105                 110

Ala Val Tyr Tyr Cys Ala Asn Gly Phe Ala Tyr Trp Gly Gln Gly Thr
        115                 120                 125

Leu Val Thr Val Ser Ala Ala Lys Thr Thr Pro Pro Ser Val Tyr Pro
    130                 135                 140

Leu Ala Pro Gly Ser Ala Ala Gly Gly Gly Ser Gly Gly Gly Gly
145                 150                 155                 160

Ser Gly Gly Gly Gly Ser Asp Val Val Met Thr Gln Thr Pro Leu Ser
                165                 170                 175

Leu Pro Val Ser Leu Gly Asp Gln Ala Ser Ile Ser Cys Arg Ser Ser
            180                 185                 190

Gln Ser Leu Leu His Ser Asn Gly Asn Thr Tyr Leu His Trp Tyr Leu
        195                 200                 205

Gln Lys Pro Gly Gln Ser Pro Glu Leu Leu Ile Tyr Lys Val Ser Asn
    210                 215                 220

Arg Phe Ser Gly Val Pro Asp Arg Phe Ser Gly Ser Gly Ser Gly Thr
225                 230                 235                 240

Asp Phe Thr Leu Lys Ile Ser Arg Val Glu Ala Glu Asp Leu Gly Val
                245                 250                 255

Tyr Phe Cys Ser Gln Ser Thr His Val Pro Leu Thr Phe Gly Ala Gly
            260                 265                 270

Thr Lys Leu Glu Leu Lys Gly Ser His His His His His Gly Ser
        275                 280                 285

Asp Tyr Lys Asp Asp Asp Lys
    290                 295

<210> SEQ ID NO 24
<211> LENGTH: 132
<212> TYPE: PRT
<213> ORGANISM: Homo sapiens

<400> SEQUENCE: 24
```

```
Glu Val Gln Leu Gln Gln Phe Gly Ala Glu Leu Val Lys Pro Gly Thr
1               5                   10                  15

Ser Val Lys Ile Ser Cys Lys Ala Ser Gly Tyr Ile Phe Thr Asp Ser
            20                  25                  30

Lys Asn Met Asp Trp Val Lys Gln Ser His Gly Lys Ser Leu Glu Trp
        35                  40                  45

Ile Gly Asp Ile Asp Pro Asn Phe Asp Ser Ser Tyr Asn Gln Lys
        50                  55                  60

Phe Lys Gly Lys Ala Thr Leu Thr Val Asp Lys Ser Ser Asn Thr Ala
65                  70                  75                  80

Tyr Met Glu Leu Arg Ser Leu Thr Ser Glu Asp Thr Ala Val Tyr Tyr
                85                  90                  95

Cys Ala Arg Gly Gly Phe Pro Tyr Gly Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro
        130
```

MATERIALS AND METHODS FOR TREATING STRESS-RELATED DISORDERS AND CANCER

CROSS-REFERENCE TO RELATED APPLICATIONS

The present application claims the benefit of priority to U.S. Provisional Application No. 62/683,369, filed Jun. 11, 2018, U.S. Provisional Application No. 62/777,572, filed Dec. 10, 2018 and U.S. Provisional Application No. 62/843,677, filed May 6, 2019, the disclosures of which are incorporated herein by reference in their entireties.

STATEMENT OF GOVERNMENT SUPPORT

This invention was made with government support under CA195563 awarded by the National Institutes of Health. The government has certain rights in the invention.

FIELD OF THE INVENTION

The present disclosure is directed to corticotropin-releasing hormone (CRH) peptide fragments, anti-CRH antibodies and the use of such peptide fragments and antibodies for the treatment of disorders associated with hypothalamic-pituitary adrenal (HPA) axis activation (e.g. stress-related disorders and cancer).

INCORPORATION BY REFERENCE OF MATERIALS SUBMITTED ELECTRONICALLY

This application contains, as a separate part of the disclosure, a Sequence Listing in computer readable form (Filename: 52978_Seqlisting.txt; Size: 15,132 bytes; Created: Jun. 7, 2019), which is incorporated by reference in its entirety.

BACKGROUND

Corticotropin-releasing hormone (CRH) is a central coordinator of the neuroendocrine and behavioral response to stressful stimuli. CRH has been evolutionarily conserved in the vertebrate lineage from a time preceding the teleosts and tetrapods, over 550 million years. This conservation across species highlights the importance of CRH in the vertebrate response to stressful stimuli.

CRH signals through its receptor the CRHR1 to control hypothalamic-pituitary-adrenal (HPA) axis activation; CRH release from the paraventricular nucleus (PVN) of the hypothalamus acts on CRHR1 receptors in the anterior pituitary, causing Adrenocorticotropic Hormone (ACTH) release that stimulates the adrenal glands to produce and release glucocorticoids (GCs), namely cortisol in humans and corticosterone in rodents. Glucocorticoids freely diffuse throughout the body and act on high affinity mineralocorticoid (MR) and low affinity glucocorticoid (GR) receptors that are expressed in almost every vertebrate cell type. MR and GR signaling cause both rapid functional responses in many cell types in addition to long-standing effects through regulation of transcription via glucocorticoid-response elements (GREs). The response to GR and MR receptor activation leads to mobilization of resources and cellular adaptations that prepare the body to overcome a stressor.

In the absence of a stressful stimulus, the PVN receives input from the suprachiasmatic nucleus (SCN) of the hypothalamus and responds to melatonin levels, altering CRH release throughout the day based on these inputs. These daily fluctuations in CRH release in turn produce the circadian rhythm of GC release, with peak levels of GCs being present at awakening and trough levels before returning to sleep.

In addition to its effects on the HPA Axis, CRH and the CRHR1 are widely expressed in many regions of the brain implicated in cognition and anxiety, including the neocortex, hippocampus, amygdala, and locus coeruleus. CRH has been shown to have region specific effects on anxiety, and is best described as a neuroregulator: augmenting the activity of CRHR1 expressing neurons but not serving as a classical neurotransmitter.

SUMMARY

In one aspect, the disclosure provides an antibody or antigen binding fragment thereof that specifically binds to a region of corticotropin-releasing hormone (CRH) comprising amino acids 1-21 of SEQ ID NO: 1. In some embodiments, the antibody or antigen binding fragment thereof comprises a set of six CDRs set forth in SEQ ID NOs: 12-17 or SEQ ID NOs: 4-9. In some embodiments, the antibody or antigen binding fragment thereof comprises a heavy chain variable region comprising an amino acid sequence set forth in SEQ ID NO: 19 or SEQ ID NO: 11. In some embodiments, the antibody or antigen binding fragment thereof comprises a light chain variable region comprising an amino acid sequence set forth in SEQ ID NO: 18 or 10.

In some embodiments, the antibody or antigen binding fragment thereof is a monoclonal antibody. In some embodiments, the antibody or antigen binding fragment thereof is a humanized antibody. In some embodiments, the antibody or antigen binding fragment thereof comprises two heavy chains and two light chains. In some embodiments, the antibody is an IgG. In some embodiments, the antigen binding fragment is a Fab fragment or an scFv. In some embodiments, the scFv comprises an amino acid sequence set forth in SEQ ID NO: 22 or SEQ ID NO: 23.

Methods of treating a disorder associated with HPA axis activation (e.g., a stress-related disorder or cancer) are contemplated. For example, in some embodiments, described herein is a method of treating a stress-related disorder. In this regard, the method comprises administering to a subject in need thereof an antibody or antigen binding fragment thereof described herein in an amount effective to treat the disorder. Exemplary stress-related disorders include, but are not limited to, anxiety, depression, Alzheimer's Disease, post traumatic stress disorder, generalized anxiety disorder, major depression, anorexia nervosa, post-traumatic stress disorder, adrenal disorder, metabolic syndrome, type 1 diabetes, sarcopenia and multiple sclerosis.

Methods of inducing an immune response to corticotropin releasing hormone (CRH) in a subject are also contemplated. In this regard, the method comprises administering to a subject in need thereof an amino terminal peptide fragment of CRH in an amount effective to induce an immune response in the subject. In some embodiments, the amino terminal fragment of CRH consists of an amino acid sequence set forth in SEQ ID NO: 2. In some embodiments, the amino terminal fragment of CRH consists of an amino acid sequence set forth in SEQ ID NO: 3. In some embodiments, the peptide fragment is conjugated to a T cell reactive epitope (e.g., tetanus toxoid). Optionally, the method further comprises administering an adjuvant to the subject.

Also contemplated are methods of treating a stress-related disorder in a subject in need thereof comprising administering to the subject an amino terminal peptide fragment of CRH in an amount effective to treat the disorder in the subject.

Also contemplated is a method of treating cancer in a subject in need thereof, comprising administering to the subject an anti-CRH antibody described herein in combination with an immunotherapeutic. In some embodiments, the immunotherapeutic is a checkpoint inhibitor. In some embodiments, the immunotherapeutic is an anti-PD1 antibody.

BRIEF DESCRIPTION OF THE FIGURES

In FIG. 1A, the first set of five bars on the graph are mouse I44, the second set of five bars on the graph are mouse I45 and the last set of five bars are mouse I46. In FIG. 1B, the first set of four bars are mouse 96, the second set of four bars are from mouse 97, the third set of four bars from mouse 98, the fourth set of four bars are from mouse 99, the fifth set of four bars are from mouse 100, the sixth set of four bars are from mouse 144 and the seventh set of four bars are from mouse 146.

FIG. 5 provides the variable region sequences of anti-CRH antibodies A and B and the sequence of the N-terminal CRH peptide used to produce the antibodies.

FIG. 6 provides a bar graph showing the results of an ELISA binding assay testing the binding of generated anti-CRH ScFv's to CRH. Relative absorbance (y-axis) is provided for lysate of untransfected HEK-293 cells, lysate of cells transduced with a DNA construct encoding an ScFv comprising Antibody A variable regions, untransfected cell lysate, and lysate of cells transduced with a DNA construct encoding an ScFv comprising Antibody B variable regions (x-axis).

FIG. 7 provides an alignment of the mouse variable region (SEQ ID NO: 19) of anti-CRH Antibody B and a similar human variable framework (SEQ ID NO: 24) for humanization of the antibody. CDRs are highlighted.

FIG. 8 provides a bar graph showing that Antibody B reduced CRH-induced increases in cyclic AMP in vitro.

FIG. 9 provides graphs showing that mice under mild stress treated with Antibody B (anti-CRH demonstrated a dose-response effect to reduce corticosterone levels.

FIG. 10 provides the protocol for the chronic variable stress experiments describer in Example 10.

FIG. 12A is a volcano plot showing significantly changed genes. FIG. 12B is a graph showing the results of weighted correlation network (WGCN) analysis reveals networks of associated changed genes.

FIGS. 13A-B are graphs showing the significant increase in the amount of live splenocytes and trending increase in spleen weight with treatment with Antibody B. FIGS. 13B-Q: In addition, it was determined that there was a significant increase in the percentage of B cells and decrease in the percentage of T cells, FIGS. 13O-Q NK Cells, and FIGS. 13L-N inflammatory monocytes among these live splenocytes, but with (FIG. 13G and FIG. 13J) increases in the absolute numbers of both B and T cells.

FIG. 16 shows the Octet red Biolayer interferometry calculating dissociation constant of Kd=4.0E-9 for Antibody B to the UCN2 peptide. This affinity is 4000 times lower than the affinity of the Antibody B to CRF peptide.

DETAILED DESCRIPTION

Figure 1:
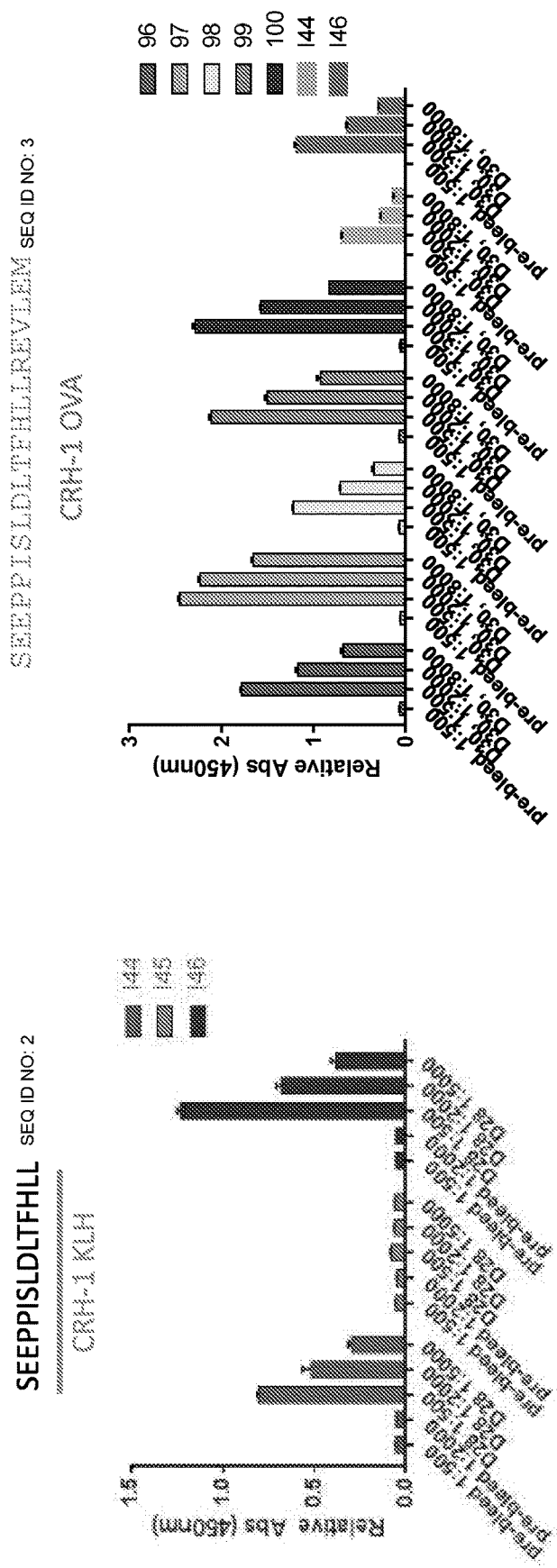
FIGS. 1A and 1B are bar graphs showing that vaccination with amino terminal fragments of corticotropin releasing hormone (CRH) (SEQ ID NOs: 2 and 3) generated anti-CRH antibodies in mice (y-axis, relative absorbance; x-axis, serum dilution).
Figure 2:
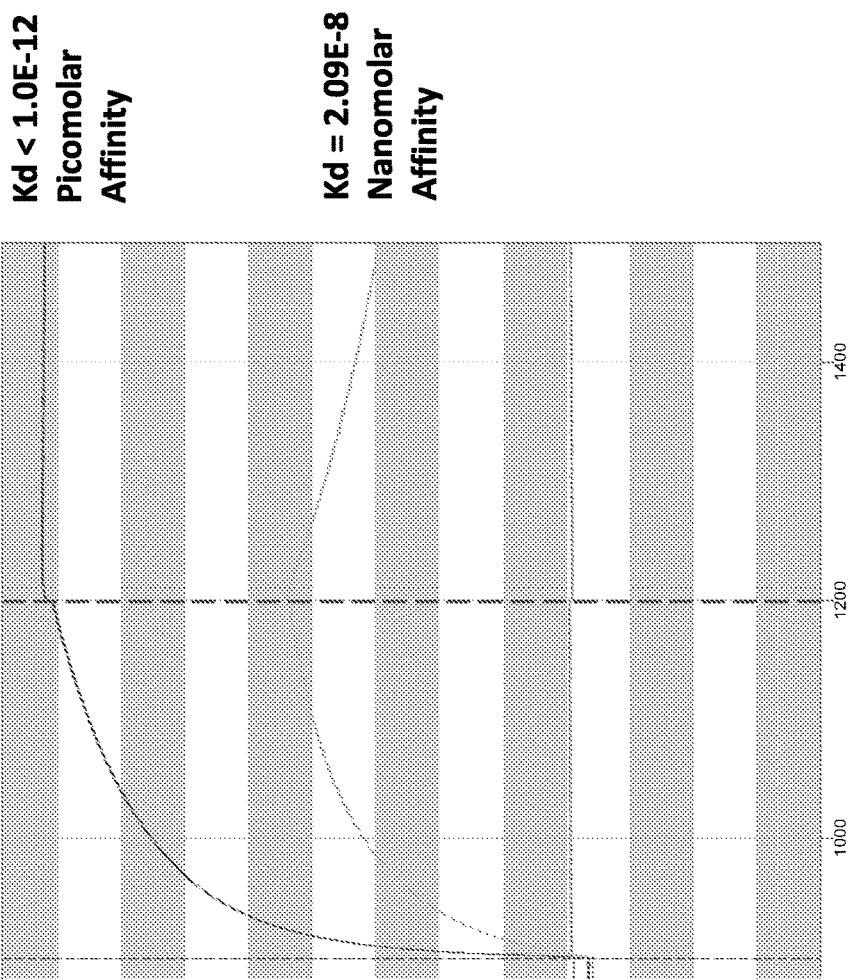
FIG. 2 is a graph showing the affinity of isolated monoclonal antibodies to CRH.
Figure 3B:
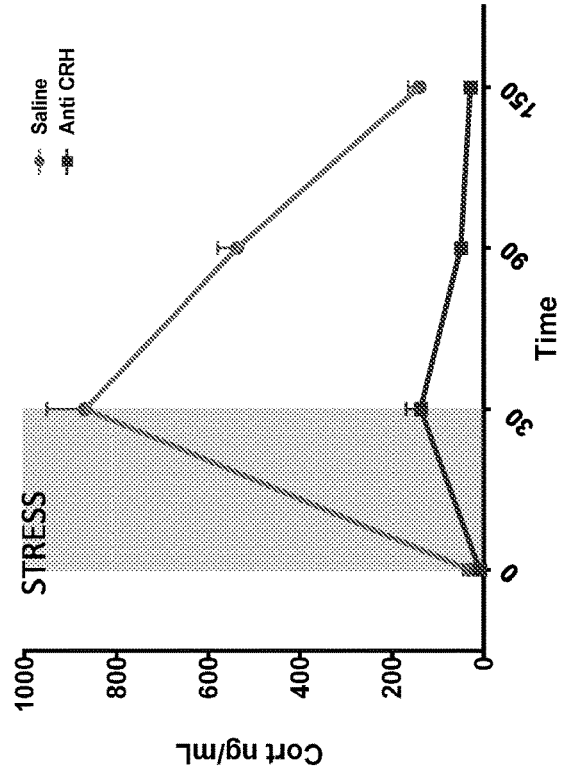
FIGS. 3A and 3B are graphs showing the effect of the anti-CRH antibodies on acute stress (y-axis, corticosterone (ng/mL); x-axis, time of plasma draw).
Figure 3A:
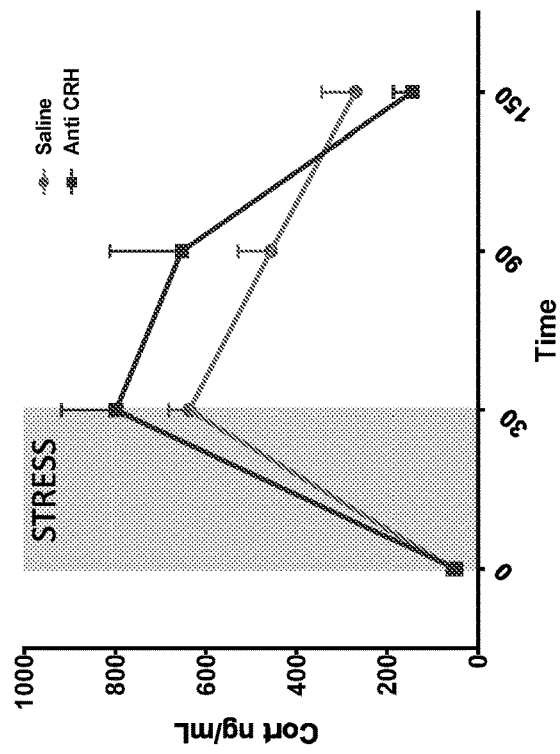

The present disclosure is based in part on the discovery that in vivo administration of an anti-corticotropin releasing hormone (CRH) antibody inhibits a corticosterone response to acute stress.

Corticotropin-releasing hormone (CRH) is a 41-amino acid peptide (SEEPPISLDLTFHLLREVLE-MARAEQLAQQAHSNRKLMEII (SEQ ID NO: 1)) derived from a 196-amino acid preprohormone (Genbank Accession No. EAW86897.1). CRH is secreted by the paraventricular nucleus (PVN) of the hypothalamus in response to stress. Increased CRH production has been observed to be associated with Alzheimer's disease and major depression (Raadsheer et al., Am J Psychiatry. 152 (9): 1372-6, 1995), and autosomal recessive hypothalamic corticotropin deficiency has multiple (and potentially fatal) metabolic consequences, including hypoglycemia.

As described in Example 1, CRH peptide fragments (e.g., amino terminal fragments) were used to generate anti-CRH antibodies in vivo by active immunization. In this regard, the use of CRH peptide fragments to generate an immune response to CRH (e.g., generate anti-CRH antibodies) in a subject is specifically contemplated. The term "amino terminal fragment" as used herein means a truncated form of CRH that retains a stretch of amino acids at the N-terminus and lacks a stretch of amino acids at the C-terminus of the CRH of SEQ ID NO: 1. In some embodiments, the CRH peptide fragment comprises a peptide comprising 30 amino acids or less of the amino acid sequence set forth in SEQ ID NO: 1. In some embodiments, the CRH peptide fragment comprises a peptide that is 10, 11, 12, 13, 14, 15, 16, 17, 18, 19, 20, 21, 22, 23, 24, 25, 26, 27, 28, 29 or 30 amino acids in length. In some embodiments, the CRH peptide fragment is less than 25 amino acids in length. In some embodiments, the CRH peptide fragment is 10 amino acids in length. In various aspects, the CRM peptide fragment is an amino terminal CRM peptide fragment comprising no more than the first 30 amino acids of SEQ ID NO: 1. In some embodiments, the CRH peptide fragment comprises amino acids 1-15 of SEQ ID NO: 1 (i.e., SEQ ID NO: 2). In some embodiments, the CRH peptide fragment comprises amino acids 1-21 of SEQ ID NO: 1 (i.e., SEQ ID NO: 3).

In some embodiments, the CRH peptide comprises an amino acid sequence at least 85% (or at least 90%, at least 91%, at least 92%, at least 93%, at least 94%, at least 95%, at least 96%, at least 97%, at least 99%) identical to the amino acid sequence set forth in SEQ ID NO: 2. In some embodiments, the CRH peptide comprises an amino acid sequence at least 85% (or at least 90%, at least 91%, at least 92%, at least 93%, at least 94%, at least 95%, at least 96%, at least 97%, at least 99%) identical to the amino acid sequence set forth in SEQ ID NO: 3.

In some embodiments, the CRH peptide is conjugated to Keyhole Limpet Hemocyanin (KLH) or ovalbumin (OVA).

In some embodiments, the CRH peptide fragment is administered together with an adjuvant. As used herein, the term "adjuvant" refers to a compound that, when used in combination with the peptide, augments or otherwise alters the immune response induced against the peptide. Modification of the immune response may include intensification or broadening the specificity of antibody and/or cellular immune responses. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Examples of known adjuvants include complete Freund's adjuvant (a non-specific stimulator of the immune response containing killed *Mycobacterium tuberculosis*), incomplete Freund's adjuvants and aluminum hydroxide adjuvant. Other known adjuvants include granulocyte macrophage colony-stimulating factor (GMCSP), *Bacillus* Calmette-Guerin (BCG), aluminum hydroxide, Muramyl dipeptide (MDP) compounds (such as thur-MDP and nor-MDP), muramyl tripeptide phosphatidylethanolamine (MTP-PE), RIBI's adjuvants (Ribi ImmunoChem Research, Inc., Hamilton Mont., which contains three components extracted from bacteria), trehalose dimycolate (TDM) and cell wall skeleton (CWS) in a 2% squalene/Tween 80 emulsion. MF-59, Novasomes®, and major histocompatibility complex (MHC) antigens are other known adjuvants.

Antibodies

The disclosure also provides anti-CRH antibodies. The term "antibody" refers to an intact immunoglobulin molecule (including polyclonal, monoclonal, chimeric, humanized, and/or human versions having full length heavy and/or light chains). The antibody may be any type of antibody, i.e., immunoglobulin, known in the art. In exemplary embodiments, the antibody is an antibody of class or isotype IgA, IgD, IgE, IgG, or IgM. In exemplary embodiments, the antibody described herein comprises one or more alpha, delta, epsilon, gamma, and/or mu heavy chains. In exemplary embodiments, the antibody described herein comprises one or more kappa or light chains. In exemplary aspects, the antibody is an IgG antibody and optionally is one of the four human subclasses: IgG1, IgG2, IgG3 and IgG4. Also, the antibody in some embodiments is a monoclonal antibody. In other embodiments, the antibody is a polyclonal antibody. In some aspects, the antibody is a chimeric or a humanized antibody. The term "humanized" when used in relation to antibodies refers to antibodies having at least CDR regions from a non-human source and which are engineered to have a structure and immunological function more similar to true human antibodies than the original source antibodies. For example, humanizing can involve grafting CDRs from a non-human antibody, such as a mouse antibody, into a human antibody framework. Humanizing also can involve select amino acid substitutions to make a non-human sequence look more like a human sequence.

In some aspects, the antibody is a Humaneered™ antibody. Humaneering technology converts non-human antibodies into engineered human antibodies. Humaneered™ antibodies have high affinity, and are highly similar to human germline antibody sequences. See, e.g., Tomasevic et al., Growth Factors 32: 223-235 (2014).

"Specifically binds" as used herein means that the antibody (or antigen binding fragment) preferentially binds an antigen (CRH peptide) over other proteins. In some embodiments, "specifically binds" means the antibody has a higher affinity for the antigen than for other proteins. Antibodies that specifically bind an antigen may have a binding affinity for the antigen of less than or equal to $1\times10^{-7}$ M, less than or equal to $2\times10^{-7}$ M, less than or equal to $3\times10^{-7}$ M, less than or equal to $4\times10^{-7}$ M, less than or equal to $5\times10^{-7}$ M, less than or equal to $6\times10^{-7}$ M, less than or equal to $7\times10^{-7}$ M, less than or equal to $8\times10^{-7}$ M, less than or equal to $9\times10^{-7}$ M, less than or equal to $1\times10^{-8}$ M, less than or equal to $2\times10^{-8}$ M, less than or equal to $3\times10^{-8}$ M, less than or equal to $4\times10^{-8}$ M, less than or equal to $5\times10^{-8}$ M, less than or equal to $6\times10^{-8}$ M, less than or equal to $7\times10^{-8}$ M, less than or equal to $8\times10^{-8}$ M, less than or equal to $9\times10^{-8}$ M, less than or equal to $1\times10^{-9}$ M, less than or equal to $2\times10^{-9}$ M, less than or equal to $3\times10^{-9}$ M, less than or equal to $4\times10^{-9}$ M, less than or equal to $5\times10^{-9}$ M, less than or equal to $6\times10^{-9}$ M, less than or equal to $7\times10^{-9}$ M, less than or equal to $8\times10^{-9}$ M, less than or equal to $9\times10^{-9}$ M, less than or equal to $1\times10^{-10}$ M, less than or equal to $2\times10^{-10}$ M, less than or equal to $3\times10^{-10}$ M, less than or equal to $4\times10^{-10}$ M, less than or equal to $5\times10^{-10}$ M, less than or equal to $6\times10^{-10}$ M, less than or equal to $7\times10^{-10}$ M, less than or equal to $8\times10^{-10}$ M, less than or equal to $9\times10^{-10}$ M, less than or equal to $1\times10^{-11}$ M, less than or equal to $2\times10^{-11}$ M, less than or equal to $3\times10^{-11}$ M, less than or equal to $4\times10^{-11}$ M, less than or equal to $5\times10^{-11}$ M, less than or equal to $6\times10^{-11}$ M, less than or equal to $7\times10^{-11}$ M, less than or equal to $8\times10^{-11}$ M, less than or equal to $9\times10^{-11}$ M, less than or equal to $1\times10^{-12}$ M, less than or equal to $2\times10^{-12}$ M, less than or equal to $3\times10^{-12}$ M, less than or equal to $4\times10^{-12}$ M, less than or equal to $5\times10^{-12}$ M, less than or equal to $6\times10^{-12}$ M, less than or equal to $7\times10^{-12}$ M, less than or equal to $8\times10^{-12}$ M, or less than or equal to $9\times10^{-12}$ M. It will be appreciated that ranges having the values above as end points is contemplated in the context of the disclosure. For example, the antibody or antigen binding fragment thereof may bind CRH of SEQ ID NO: 1 with an affinity of about $1\times10^{-7}$ M to about $9\times10^{-12}$ M or an affinity of $1\times10^{-9}$ to about $9\times10^{-12}$.

In some or any embodiments, the antibody (or antigen binding fragment) binds to CRH of SEQ ID NO: 1, or a naturally occurring variant thereof, with an affinity (Kd) of less than or equal to $1\times10^{-7}$ M, less than or equal to $1\times10^{-8}$ M, less than or equal to $1\times10^{-9}$ M, less than or equal to $1\times10^{-10}$ M, less than or equal to $1\times10^{-11}$ M, or less than or equal to $1\times10^{-12}$ M, or ranging from $1\times10^{-9}$ to $1\times10^{-10}$, or ranging from $1\times10^{-12}$ to about $1\times10^{-13}$. Affinity is determined using a variety of techniques, examples of which include an affinity ELISA assay and a surface plasmon resonance (BIAcore) assay.

In some or any embodiments, the antibody (or antigen binding fragment thereof) binds to a CRH peptide comprising amino acids 1-21 of SEQ ID NO: 1, with any of the affinities described above. Alternatively, or in addition, the antibody (or antigen binding fragment thereof) binds to a CRH peptide comprising amino acids 1-15 of SEQ ID NO: 1, with any of the affinities described above.

"CDR" refers to the complementarity determining region within antibody variable sequences. There are three CDRs in each of the variable regions of the heavy chain and the light chain, which are designated CDR1, CDR2 and CDR3, for each of the variable regions. The term "set of six CDRs" as used herein refers to a group of three CDRs that occur in the light chain variable region and heavy chain variable region, which are capable of binding the antigen. The exact boundaries of CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):73245 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDRs are obtained by, e.g., constructing polynucleotides that encode the CDR of interest and expression in a suitable host cell. Such polynucleotides are prepared, for example, by using the polymerase chain reaction to synthesize the variable region using mRNA of antibody-producing cells as a template (see, for example, Larrick et al., *Methods: A Companion to Methods in Enzymology*, 2:106 (1991); Courtenay-Luck, "Genetic Manipulation of Monoclonal Antibodies," in *Monoclonal Antibodies Production, Engineering and Clinical Application*, Ritter et al. (eds.), page 166, Cambridge University Press (1995); and Ward et al., "Genetic Manipulation and Expression of Antibodies," in *Monoclonal Antibodies: Principles and Applications*, Birch et al., (eds.), page 137, Wiley-Liss, Inc. (1995)).

In various aspects, the antibody (or antigen binding fragment thereof) comprises at least one CDR sequence having at least 75% identity (e.g., at least 75%, 80%, 85%, 90%, 95% or 100% identity) to a CDR selected from CDR-H1, CDR-H2, CDR-H3, CDR-L1, CDR-L2, and CDR-L3 wherein CDR-H1 has the sequence given in SEQ ID NO: 4, CDR-H2 has the sequence given in SEQ ID NO: 5, CDR-H3 has the sequence given in SEQ ID NO: 6, CDR-L1 has the sequence given in SEQ ID NO: 7, CDR-L2 has the sequence given in SEQ ID NO: 8 and CDR-L3 has the sequence given in SEQ ID NO: 9. The anti-CRH antibody, in various aspects, comprises two of the CDRs, three of the CDRs, four of the CDRs, five of the CDRs or all six of the CDRs. In a preferred embodiment, the anti-CRH antibody comprises a set of six CDRs as follows: CDR-H1 of SEQ ID NO: 4, CDR-H2 of SEQ ID NO: 5, CDR-H3 of SEQ ID NO: 6, CDR-L1 of SEQ ID NO: 7, CDR-L2 of SEQ ID NO: 8 and CDR-L3 of SEQ ID NO: 9.

In various aspects, the antibody (or antigen binding fragment thereof) comprises at least one CDR sequence having at least 75% identity (e.g., at least 75%, 80%, 85%, 90%, 95% or 100% identity) to a CDR selected from CDR-H1, CDR-H2, CDR-H3, CDR-L1, CDR-L2, and CDR-L3 wherein CDR-H1 has the sequence given in SEQ ID NO: 12, CDR-H2 has the sequence given in SEQ ID NO: 13, CDR-H3 has the sequence given in SEQ ID NO: 14, CDR-L1 has the sequence given in SEQ ID NO: 15, CDR-L2 has the sequence given in SEQ ID NO: 16 and CDR-L3 has the sequence given in SEQ ID NO: 17. The anti-CRH antibody, in various aspects, comprises two of the CDRs, three of the CDRs, four of the CDRs, five of the CDRs or all six of the CDRs. In a preferred embodiment, the anti-CRH antibody comprise a set of six CDRs as follows: CDR-H1 of SEQ ID NO: 12, CDR-H2 of SEQ ID NO: 13, CDR-H3 of SEQ ID NO: 14, CDR-L1 of SEQ ID NO: 15, CDR-L2 of SEQ ID NO: 16 and CDR-L3 of SEQ ID NO: 17.

In some or any embodiments, the antibody comprises a light chain variable region comprising an amino acid sequence having at least 75% identity (e.g., at least 75%, 80%, 85%, 90%, 95% or 100% identity) to the amino acid sequence set forth in SEQ ID NO: 10 and/or a heavy chain variable region comprising an amino acid sequence having at least 75% identity (e.g., at least 75%, 80%, 85%, 90%, 95% or 100% identity) to the amino acid sequence set forth in SEQ ID NO: 11. In various aspects, the difference in the sequence compared to SEQ ID NO: 10 or 11 lies outside the CDR region in the corresponding sequences. In some or any embodiments, the antibody (or antigen binding fragment) comprises a light chain variable region comprising an amino acid sequence set forth in SEQ ID NO: 10 and a heavy chain variable region comprising an amino acid sequence set forth in SEQ ID NO: 11. In some or any embodiments, the antibody (or antigen binding fragment) comprises a light chain variable region encoded by the nucleotide sequence set forth in SEQ ID NO: 22. In some or any embodiments, the antibody (or antigen binding fragment) comprises a heavy chain variable region encoded by the nucleotide sequence set forth in SEQ ID NO: 23.

In some or any embodiments, the antibody comprises a light chain variable region comprising an amino acid sequence having at least 75% identity (e.g., at least 75%, 80%, 85%, 90%, 95% or 100% identity) to the amino acid sequence set forth in SEQ ID NO: 18 and/or a heavy chain variable region comprising an amino acid sequence having at least 75% identity (e.g., at least 75%, 80%, 85%, 90%, 95% or 100% identity) to the amino acid sequence set forth in SEQ ID NO: 19. In various aspects, the difference in the sequence compared to SEQ ID NO: 18 or 19 lies outside the CDR region in the corresponding sequences. In some or any embodiments, the antibody (or antigen binding fragment thereof) comprises a light chain variable region comprising an amino acid sequence set forth in SEQ ID NO: 18 and a heavy chain variable region comprising an amino acid sequence set forth in SEQ ID NO: 19.

Antigen binding fragments of the anti-CRH antibodies described herein are also contemplated. The antigen binding fragment can be any part of an antibody that has at least one antigen binding site, and the antigen binding fragment may be part of a larger structure (an "antibody product") that retains the ability of the antigen binding fragment to recognize CRH. For ease of reference, these antibody products that include antigen binding fragments are included in the disclosure herein of "antigen binding fragment." Examples of antigen binding fragments, include, but are not limited to, Fab, F(ab')$_2$, a monospecific or bispecific Fab$_2$, a trispecific Fab$_3$, scFv, dsFv, scFv-Fc, bispecific diabodies, trispecific triabodies, minibodies, a fragment of IgNAR (e.g., V-NAR), a fragment of hcIgG (e.g., VhH), bis-scFvs, fragments expressed by a Fab expression library, and the like. In exemplary aspects, the antigen binding fragment is a domain antibody, VhH domain, V-NAR domain, VH domain, VL domain, or the like. Antibody fragments of the disclosure, however, are not limited to these exemplary types of antibody fragments. In exemplary aspects, antigen binding fragment is a Fab fragment. In exemplary aspects, the antigen binding fragment comprises two Fab fragments. In exemplary aspects, the antigen binding fragment comprises two Fab fragments connected via a linker. In exemplary aspects, the antigen binding fragment comprises or is a minibody comprising two Fab fragments. In exemplary aspects, the antigen binding fragment comprises, or is, a minibody comprising two Fab fragments joined via a linker. Minibodies are known in the art. See, e.g., Hu et al., Cancer Res 56: 3055-3061 (1996). In exemplary aspects, the antigen binding fragment comprises or is a minibody comprising two Fab fragments joined via a linker, optionally, comprising an alkaline phosphatase domain.

A domain antibody comprises a functional binding unit of an antibody, and can correspond to the variable regions of either the heavy (VH) or light (VL) chains of antibodies. A domain antibody can have a molecular weight of approximately 13 kDa, or approximately one-tenth of a full antibody. Domain antibodies may be derived from full antibodies such as those described herein.

In some embodiments, the scFv is attached to a human Fc domain. In some embodiments, the Fc domain does not activate Fc effector functions.

Methods of Antibody or Antigen Binding Fragment Production

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, 5th Ed., Garland Publishing, New York, N.Y. (2001)). Monoclonal antibodies for use in the methods of the disclosure may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1). Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991). If the full sequence of the antibody or antigen-binding fragment is known, then methods of producing recombinant proteins may be employed. See, e.g., "Protein production and purification" Nat Methods 5(2): 135-146 (2008). In some embodiments, the antibodies (or antigen binding fragments) are isolated from cell culture or a biological sample if generated in vivo.

Phage display also can be used to generate the antibody of the present disclosures. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403, 484; 5,571,698; 5,837,500; 5,702,892. The techniques described in U.S. Pat. Nos. 5,780,279; 5,821,047; 5,824, 520; 5,855,885; 5,858,657; 5,871,907; 5,969,108; 6,057, 098; and 6,225,447.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol, 235, 959-973 (1994). A preferred chimeric or humanized antibody has a human constant region, while the variable region, or at least a CDR, of the antibody is derived from a non-human species. Methods for humanizing non-human antibodies are well known in the art. (See U.S. Pat. Nos. 5,585,089, and 5,693,762.)

Techniques developed for the production of "chimeric antibodies," e.g., the splicing of mouse antibody genes to human antibody genes to obtain a molecule with appropriate antigen specificity and biological activity, can be used (Morrison et al., Proc Natl Acad Sci 81: 6851-6855 (1984); Neuberger et al., Nature 312: 604-608 (1984); Takeda et al., Nature 314: 452-454 (1985)). Alternatively, techniques described for the production of single chain antibodies (U.S. Pat. No. 4,946,778) can be adapted to produce CRH-specific single chain antibodies.

Likewise, using techniques known in the art to isolate CDRs, compositions comprising CDRs are generated. Compositions comprising one, two, and/or three CDRs of a heavy chain variable region or a light chain variable region of a monoclonal antibody can be generated. The CDRs of exemplary antibodies are provided herein as SEQ ID NOs: 4-9 and 12-17. Techniques for cloning and expressing nucleotide and polypeptide sequences are well-established in the art (see, e.g., Sambrook et al., Molecular Cloning: A Laboratory Manual, 2nd Edition, Cold Spring Harbor, N.Y. (1989)). The amplified CDR sequences are ligated into an appropriate expression vector. The vector comprising one, two, three, four, five and/or six cloned CDRs optionally contains additional polypeptide encoding regions linked to the CDR.

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701 (1984); Titus et al., J. Immunol., 138:4018-22 (1987)).

Methods of testing antibodies for the ability to bind to an epitope of CRH, regardless of how the antibodies are produced, are known in the art and include, e.g., radioimmunoassay (RIA), ELISA, Western blot, immunoprecipitation, surface plasmon resonance (e.g., BIAcore), and competitive inhibition assays (see, e.g., Janeway et al., infra, and U.S. Patent Application Publication No. 2002/0197266).

Antibody fragments that contain the antigen binding, or idiotype, of the antibody molecule may be generated by techniques known in the art. For example, a F(ab')2 fragment may be produced by pepsin digestion of the antibody molecule; Fab' fragments may be generated by reducing the disulfide bridges of the F(ab')$_2$ fragment; and two Fab' fragments which may be generated by treating the antibody molecule with papain and a reducing agent. The disclosure is not limited to enzymatic methods of generating antigen binding fragments; the antigen binding fragment may be a recombinant antigen binding fragment produced by expressing a polynucleotide encoding the fragment in a suitable host cell.

A single-chain variable region fragments (scFv), which consists of a truncated Fab fragment comprising the variable (V) domain of an antibody heavy chain linked to a V domain of an antibody light chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., *Biomol Eng.* 2001 18:95-108, (2001) and Todorovska et al., *J Immunol Methods.* 248:47-66, (2001).

Detection Methods

It is sometimes desirable to detect the presence or measure the amount of CRH in a sample. In this regard, the disclosure provides a method of using the antibody or fragment thereof described herein to measure the amount of CRH in a sample. To determine a measurement of CRH, a biological sample from a mammalian subject is contacted with an anti-CRH antibody (or antigen binding fragment thereof) described herein for a time sufficient to allow immunocomplexes to form. Immunocomplexes formed between the antibody and CRH in the sample are then detected. The amount of CRH in the biological sample is optimally quantitated by measuring the amount of the immunocomplex formed between the antibody and the CRH. For example, the antibody can be quantitatively measured if it has a detectable label, or a secondary antibody can be used to quantify the immunocomplex.

In some embodiments, the biological sample comprises a tissue sample, a cell sample, or a biological fluid sample, such as blood, saliva, serum, or plasma.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats can readily be adapted to employ the antibodies (or fragments thereof) of the present disclosure. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test sample used in the above-described method will vary based on the assay format, nature of the detection method and the tissues, cells or fluids used as the sample to be assayed.

The assay described herein may be useful in, e.g., evaluating the efficacy of a particular therapeutic treatment regime in animal studies, in clinical trials, or in monitoring the treatment of an individual patient.

In some embodiments, the CRH or the anti-CRH antibody (or fragment thereof) is attached to a solid support, and binding is detected by detecting a complex between the CRH and the antibody (or fragment thereof) on the solid support. The antibody (or fragment thereof) optionally comprises a detectable label and binding is detected by detecting the label in the CRH-antibody complex.

Detection of the presence or absence of a CRH-antibody complex be achieved using any method known in the art. For example, the transcript resulting from a reporter gene transcription assay of a CRH peptide interacting with a target molecule (e.g., antibody) typically encodes a directly or indirectly detectable product (e.g., β-galactosidase activity and luciferase activity). For cell free binding assays, one of the components usually includes, or is coupled to, a detectable label. A wide variety of labels can be used, such as those that provide direct detection (such as radioactivity, luminescence, optical or electron density) or indirect detection (such as epitope tag such as the FLAG epitope, enzyme tag such as horseradish peroxidase). The label can be bound to the antibody, or incorporated into the structure of the antibody.

A variety of methods can be used to detect the label, depending on the nature of the label and other assay components. For example, the label can be detected while bound to the solid substrate or subsequent to separation from the solid substrate. Labels can be directly detected through optical or electron density, radioactive emissions, nonradiative energy transfers or indirectly detected with antibody conjugates, or streptavidin-biotin conjugates. Methods for detecting the labels are well known in the art.

Pharmaceutical Compositions

For all protein-based therapeutics described herein (e.g., antibodies) administration by the delivery of gene expression constructs are contemplated as one embodiment. Any suitable vector may be used to introduce a polynucleotide that encodes a protein-based therapeutic described herein, into the host. Exemplary vectors that have been described in the literature include replication deficient retroviral vectors, including but not limited to lentivirus vectors [Kim et al., J. Virol., 72(1): 811-816 (1998); Kingsman & Johnson, Scrip Magazine, October, 1998, pp. 43 46.]; adeno-associated viral (AAV) vectors [U.S. Pat. Nos. 5,474,935; 5,139,941; 5,622,856; 5,658,776; 5,773,289; 5,789,390; 5,834,441; 5,863,541; 5,851,521; 5,252,479; Gnatenko et al., J. Invest. Med., 45: 87 98 (1997)]; adenoviral (AV) vectors [See, e.g., U.S. Pat. Nos. 5,792,453; 5,824,544; 5,707,618; 5,693,509; 5,670,488; 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a vaccinia viral or a herpesviral (see for example, U.S. Pat. Nos. 5,879,934; 5,849,571; 5,830,727; 5,661,033; 5,328, 688; Lipofectin mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in their entirety. Replication deficient adenoviral vectors constitute a preferred embodiment.

Pharmaceutical compositions comprising an anti-CRH antibody or antigen-binding fragment thereof (or CRH peptide fragment) described herein are also contemplated. In some embodiments, the pharmaceutical composition contains formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, methionine or lysine); antimicrobials; antioxidants (such as reducing agents, oxygen/free-radical scavengers, and chelating agents (e.g., ascorbic acid, EDTA, sodium sulfite or sodium hydrogen-sulfite)); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter-ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

Selection of the particular formulation materials described herein may be driven by, for example, the intended route of administration, delivery format and desired dosage. See, for example, REMINGTON'S PHARMACEUTICAL SCIENCES, supra. The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments, the composition may be prepared for storage by mixing the selected composition having the desired degree of purity with optional formulation agents (REMINGTON'S PHARMACEUTICAL SCIENCES, supra) in the form of a lyophilized cake or an aqueous solution. Further, in some embodiments, the antibody or (antigen binding fragment thereof) may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the composition may be provided in the form of a pyrogen-free, parenterally acceptable aqueous solution comprising the desired antibody or fragment in a pharmaceutically acceptable vehicle. A particularly suitable vehicle for parenteral injection is sterile distilled water in which the antibody or fragment is formulated as a sterile, isotonic solution, properly preserved. In certain embodiments, implantable drug delivery devices may be used to introduce the desired antibody (or antigen binding fragment thereof).

Additional pharmaceutical compositions will be evident to those skilled in the art, including formulations involving antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP133988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP036676; EP088046 and EP143949, incorporated by reference.

Embodiments of the antibody formulations can further comprise one or more preservatives.

The therapeutically effective amount of an antibody-containing pharmaceutical composition to be employed will depend, for example, upon the therapeutic context and objectives. One skilled in the art will appreciate that the appropriate dosage levels for treatment will vary depending, in part, upon the molecule delivered, the indication(s) for which the antibody is being used, the route of administration, and the size (body weight, body surface or organ size) and/or condition (the age and general health) of the patient.

Administration of the compositions described herein will be via any common route so long as the target tissue is available via that route. The pharmaceutical compositions may be introduced into the subject by any conventional method, e.g., by intravenous, intradermal, intramuscular, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time. In some embodiments, the composition is delivered via local administration to the brain.

Therapeutic Methods

The antibodies or antigen binding fragments thereof, CRH peptide fragments and pharmaceutical compositions described herein are useful for treating or preventing disorders associated with CRH dysregulation or hypothalamic-pituitary-adrenal (HPA) axis activation (e.g., stress-related disorders and/or cancer). The HPA axis includes positive and negative feedback interactions among three endocrine glands: the hypothalamus, the pituitary gland, and the adrenal glands that form the neuroendocrine system. Hormones released by the endocrine glands control reactions to stress, regulation of body processes like digestion, the immune system, mood and emotions, sexuality and energy storage and expenditure. The HPA axis is dysregulated in several psychiatric and neuropsychiatric diseases, as well as in alcoholism and stroke. Examples of HPA axis biomarkers include ACTH and cortisol. Cortisol inhibits secretion of corticotropin-releasing hormone (CRH), resulting in feedback inhibition of ACTH secretion. This normal feedback loop may break down when humans are exposed to chronic stress, and may be an underlying cause of depression.

Chronic psychological stress and perturbation of the HPA-axis have been associated with many diseases and conditions including, but not limited to, Alzheimer's disease, anxiety disorders, major depression, post-traumatic stress disorder, addiction, metabolic syndrome, osteoporosis and sarcopenia. Further, chronic stress, HPA-axis dysfunction, and elevated cortisol have been implicated as an accelerant with regard to the negative physiological consequences of aging. Treatment of one or more of these disorders/conditions by administering an anti-CRH antibody described herein to a subject in need thereof is specifically contemplated.

By "treatment" or "treating" it is meant that at least an amelioration of one or more symptoms associated with retina-related disease afflicting the patient, where amelioration is used in a broad sense to refer to at least a reduction in the magnitude of a parameter, e.g., a symptom associated with the disease being treated. As such, treatment also includes situations where a pathological condition, or at least symptoms associated therewith, is completely inhibited, e.g., prevented from happening, or stopped, e.g., terminated, such that patient no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a subject, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease. The term "preventing" does not mean that 100% inhibition of the disease.

Chronic stress has been associated with a number of behavioral and physiologic morbidities. Psychological stress contributes to numerous behavioral or psychiatric conditions including, but not limited to, generalized anxiety disorder, panic disorder, major depression, Alzheimer's disease, and post-traumatic stress disorder (PTSD). Chronic stress also has also been shown to have adverse cardiovascular and immunologic effects. CRH is the main coordinator of the HPA stress response and is strongly implicated in animal models of anxiety, addiction, major depression and PTSD. Further, Alzheimer's disease stress and CRH are powerful accelerants of both amyloid and tau pathologies, and CRH drives amyloid pathology in preclinical models of Alzheimer's disease. Thus, the disclosure contemplates a method of treating or preventing anxiety, depression, Alzheimer's Disease, post traumatic stress disorder, generalized anxiety disorder, major depression, anorexia nervosa, post-traumatic stress disorder, adrenal disorder, metabolic syndrome, type 1 diabetes, sarcopenia and multiple sclerosis.

CRH has been detected in cancer tissues and cell lines and may stimulate cell motility and invasiveness of MCF7 breast cancer cells (Androulidaki et al., Mol. Cancer, 8:30, 2009). Thus, the disclosure contemplates a method of treating cancer in a subject in need thereof. Exemplary cancers include, but are not limited to, esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer (NSCLC), squamous cell non-small cell lung cancer, breast cancer, recurrent metastatic breast cancer, hepatocellular carcinoma, Hodgkin's lymphoma, follicular lymphoma, non-Hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent Ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

In some embodiments, an anti-CRH antibody described herein is administered to subject suffering from colon cancer, breast cancer or brain cancer.

It is contemplated that the methods herein reduce tumor burden, and/or reduce metastasis in the subject, and/or reduce or prevent the recurrence of tumors once the cancer has gone into remission. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

In some embodiments, one or more doses of the antibody or antigen binding fragment (or CRH peptide fragment) are administered in an amount and for a time effective to reduce or inhibit corticosterone response to stress, treat or prevent a stress-related disorder, treat cancer, reduce tumor burden or, in the case of CRH peptide fragment, induce an immune response to CRH. For example, one or more administrations of an antibody or antigen binding fragment thereof (or CRH peptide fragment) described herein are optionally carried out over a therapeutic period of, for example, about 1 week to about 24 months (e.g., about 1 month to about 12 months, about 1 month to about 18 months, about 1 month to about 9 months or about 1 month to about 6 months or about 1 month to about 3 months). In some embodiments, a subject is administered one or more doses of an antibody or fragment thereof (or CRH peptide) described herein over a therapeutic period of, for example about 1 month to about 12 months (52 weeks) (e.g., about 2 months, about 3 months, about 4 months, about 5 months, about 6 months, about 7 months, about 8 months, about 9 months, about 10 months, or about 11 months).

It may be advantageous to administer multiple doses of the antibody or antigen binding fragment (or CRH peptide fragment) at a regular interval, depending on the therapeutic regimen selected for a particular subject. In some embodiments, the antibody or fragment thereof is administered periodically over a time period of one year (12 months, 52 weeks) or less (e.g., 9 months or less, 6 months or less, or 3 months or less). In this regard, the antibody or fragment thereof is administered to the human once every about 3 days, or about 7 days, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks, or 16 weeks, or 17 weeks, or 18 weeks, or 19 weeks, or 20 weeks, or 21 weeks, or 22 weeks, or 23 weeks, or 6 months, or 12 months.

In various embodiments, one or more doses comprising from about 50 milligrams to about 1,000 milligrams of the antibody or antigen binding fragment thereof (or CRH peptide fragment) are administered to a subject (e.g., a human subject). For example, a dose can comprise at least about 5 mg, at least about 15 mg, at least about 25 mg, at least about 50 mg, at least about 60 mg, at least about 70 mg, at least about 80 mg, at least about 90 mg, at least about 100 mg, at least about 120 mg, at least about 150 mg, at least about 200 mg, at least about 210 mg, at least about 240 mg, at least about 250 mg, at least about 280 mg, at least about 300 mg, at least about 350 mg, at least about 400 mg, at least about 420 mg, at least about 450 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg or up to about 1,000 mg of antibody. Ranges between any and all of these endpoints are also contemplated, e.g., about 50 mg to about 80 mg, about 70 mg to about 140 mg, about 70 mg to about 270 mg, about 75 mg to about 100 mg, about 100 mg to about 150 mg, about 140 mg to about 210 mg, or about 150 mg to about 200 mg, or about 180 mg to about 270 mg. The dose is administered at any interval, such as multiple times a week (e.g., twice or three times per week), once a week, once every two weeks, once every three weeks, or once every four weeks.

In some embodiments, the one or more doses can comprise between about 0.1 to about 50 milligrams (e.g., between about 5 and about 50 milligrams), or about 1 to about 100 milligrams, of antibody (or antigen binding fragment thereof or CRH peptide fragment) per kilogram of subject body weight (mg/kg). For example, the dose may comprise at least about 0.1 mg/kg, at least about 0.5 mg/kg, at least about 1 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 20 mg/kg, at least about 25 mg/kg, at least about 26 mg/kg, at least about 27 mg/kg, at least about 28 mg/kg, at least about 29 mg/kg, at least about 30 mg/kg, at least about 31 mg/kg, at least about 32 mg/kg, at least about 33 mg/kg, at least about 34 mg/kg, at least about 35 mg/kg, at least about 36 mg/kg, at least about 37 mg/kg, at least about 38 mg/kg, at least about 39 mg/kg, at least about 40 mg/kg, at least about 41 mg/kg, at least about 42 mg/kg, at least about 43 mg/kg, at least about 44 mg/kg, at least about 45 mg/kg, at least about 46 mg/kg, at least about 47 mg/kg, at least about 48 mg/kg, at least about 49 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 85 mg/kg, at least about 90 mg/kg, at least about 95 mg/kg, or up to about 100 mg/kg. Ranges between any and all of these endpoints are also contemplated, e.g., about 1 mg/kg to about 3 mg/kg, about 1 mg/kg to about 5 mg/kg, about 1 mg/kg to about 8 mg/kb, about 3 mg/kg to about 8 mg·kg, about 1 mg/kg to about 10 mg/kg, about 1 mg/kg to about 20 mg/kg, about 1 mg/kg to about 40 mg/kg, about 5 mg/kg to about 30 mg/kg, or about 5 mg/kg to about 20 mg/kg.

Combination Therapy

In various embodiments, the anti-CRH antibody or fragment thereof described herein is administered in combination with an additional therapeutic useful for treating a condition or disorder associated with HPA axis activation (e.g., cancer).

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The additional therapeutic may be other therapeutic agents, such as cytokines, growth factors, other inhibitors and antibodies to target antigens useful for treating cancer or immunological disorders, for example ipilimumab (YERVOY®, Bristol-Myers Squibb Company), an antibody to CTLA-4; bevacizumab (AVASTIN®, Genentech), an antibody to VEGF-A; erlotinib (TARCEVA®, Genentech and OSI Pharmaceuticals), a tyrosine kinase inhibitor which acts on EGFR, dasatinib (SPRYCEL®, Bristol-Myers Squibb Company), an oral Bcr-Abl tyrosone kinase inhibitor; IL-21; pegylated IFN-α2b; axitinib (INLYTA®, Pfizer, Inc.), a tyrosine kinase inhibitor; and trametinib (MEKINIST®, GlaxoSmithKline), a MEK inhibitor (Philips and Atkins, Int Immunol., 27(1):39-46 (2015) which is incorporated herein by reference).

It is contemplated that the anti-CRH antibody or antibody fragment and the additional therapeutic may be given simultaneously, in the same formulation. It is further contemplated that the anti-CRH antibody and the additional therapeutic are administered in a separate formulation and administered concurrently, with concurrently referring to agents given within 30 minutes of each other.

In another aspect, the anti-CRH antibody or fragment thereof is administered prior to administration of the additional therapeutic. Prior administration refers to administration of the anti-CRH antibody within the range of one week prior to treatment with the additional therapeutic up to 30 minutes before administration of the additional therapeutic. It is further contemplated that the anti-CRH antibody is administered subsequent to administration the additional therapeutic. Subsequent administration is meant to describe administration from 30 minutes after administration of the additional therapeutic to up to one week after administration of the additional therapeutic.

It is further contemplated that other adjunct therapies may be administered, where appropriate. For example, the patient may also be administered surgical therapy, chemotherapy, a cytotoxic agent, photodynamic therapy or radiation therapy where appropriate.

Chemotherapeutic agents contemplated for use with the agents of the present disclosure include, but are not limited to, those listed in Table I:

TABLE I

Alkylating agents
Nitrogen mustards mechlorethamine
cyclophosphamide
ifosfamide
melphalan
chlorambucil
Nitrosoureas carmustine (BCNU)
lomustine (CCNU)
semustine (methyl-CCNU)
Ethylenimine/Methyl-melamine thriethylenemelamine (TEM)
triethylene thiophosphoramide
(thiotepa)
hexamethylmelamine
(HMM, altretamine)
Alkyl sulfonates busulfan
Triazines dacarbazine (DTIC)
Antimetabolites
Folic Acid analogs methotrexate
Trimetrexate
Pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide TABLE I-continued Progestins hydroxyprogesterone caproate
medroxyprogesterone acetate
megestrol acetate Estrogens diethylstilbestrol
ethynyl estradiol/equivalents Antiestrogen tamoxifen Androgens testosterone propionate
fluoxymesterone/equivalents Antiandrogens flutamide
gonadotropin-releasing
hormone analogs
leuprolide
Nonsteroidal antiandrogens flutamide
Natural products
Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide Antibiotics actimomycin D
daunomycin (rubidomycin)
doxorubicin (adriamycin)
mitoxantroneidarubicin
bleomycin
splicamycin (mithramycin)
mitomycinC
dactinomycin
aphidicolin Enzymes L-asparaginase
L-arginase Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinum coordination complexes cisplatin
Carboplatin
oxaliplatin
Anthracenedione
mitoxantrone TABLE I-continued Substituted urea hydroxyurea
Methylhydrazine derivatives N-methylhydrazine (MIH)
procarbazine
Adrenocortical suppressant mitotane (o,p'- DDD)
ainoglutethimide Cytokines interferon ($\alpha$, $\beta$, $\gamma$)
interleukin-2

Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines Radiation X-ray
ultraviolet light
gamma radiation
visible light
infrared radiation
microwave radiation Kits Once a pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the disclosure may each contain both a first container having a dried protein and a second container having an aqueous formulation. In certain embodiments, kits containing single and multi-chambered pre-filled syringes (e.g., liquid syringes and lyosyringes) are provided.

The following Examples are provided to further illustrate aspects of the disclosure, and are not meant to constrain the disclosure to any particular application or theory of operation.

EXAMPLES

Example 1—Generation of Anti-CRH Antibodies by Active Immunization

Wild type mice were injected subcutaneously with 200 µg of an N-terminal CRH peptide fragment (either Peptide A: SEEPPISLDLTFHLL (amino acids 1-15 of SEQ ID NO: 1; or SEQ ID NO: 2) or Peptide B: SEEPPISLDLTFHLL-REVLEM (amino acids 1-21 of SEQ ID NO: 1; or SEQ ID NO: 3)) emulsified in 200 µL of Complete Freund's Adjuvant, followed by two boosts of 200 µg of peptide emulsified in Incomplete Freund's Adjuvant injected IP at two week intervals. Following the final boost, serum was collected and assayed for Anti-CRH titers via direct ELISA. See FIG. 1.

Example 2—Effect of N-Terminal CRH Peptide Fragment in Model of Acute Stress Groups of mice (n=17) were administered either CRH-OVA vaccine or OVA alone, and received two additional boosts as described in Example 1. Mice were then exposed to 90 minutes of acute restraint stress. Plasma was drawn at three time points and assayed for corticosterone levels via radioimmunoassay. The CRH active vaccine and the control blocked corticosterone response to acute stress to the same extent.

Example 3—Affinity of Anti-CRH Monoclonal Antibodies

Antibodies that bind the N-terminal CRH peptides described herein demonstrate high affinity for CRH. The anti-CRH antibody that binds SEQ ID NO:2 (Antibody A) demonstrated picomolar-level affinity for the target (Kd less than $1\times10^{-12}$). The anti-CRH antibody that binds SEQ ID NO: 3 (Antibody B) demonstrated nanomolar-level affinity for the target (Kd=$2.09\times10^{-8}$).

Example 4—Anti-CRH Antibody Blocks Corticosterone Response to Acute Stress

Figure 4:
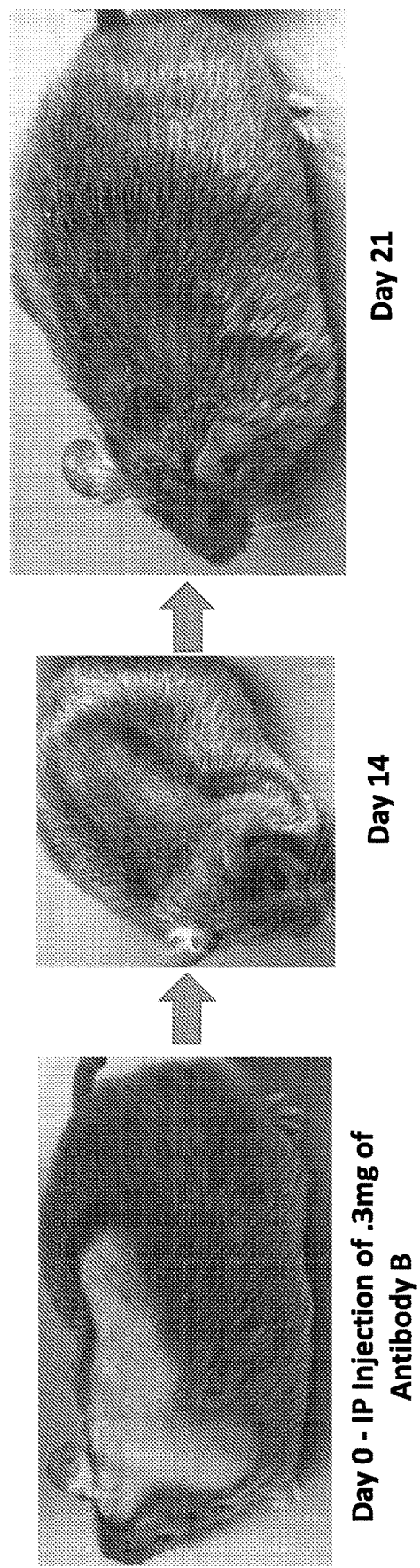
FIG. 4 contains photographs of mice injected with anti-CRH antibody B, showing that administration of anti-CRH antibody B reversed hair loss in a mouse model of Cushing's Disease.

Groups of wild-type mice (n=9) were injected intraperitoneally with 25 mg/kg of either Anti-CRH antibody A or saline 12 hours before exposure to 30 minutes of restraint stress. Plasma was drawn at four time points (0, 30, 90, and 150 minutes) and assayed for corticosterone levels via radioimmunoassay. The same experiment was repeated with anti-CRH antibody B, except a larger group of wild-type mice was utilized (n=10). As shown in FIG. 4B, anti-CRH antibody B blocked corticosterone response to acute stress. Antibody B administration reduced the level corticosterone at least four-fold at 30 minutes, the timepoint at which restraint stress was removed and corticosterone levels were at their highest in control mice.

Example 5—Anti-CRH Antibody Reversed Hair Loss in Animal Model of Cushing's Disease A wild-type mouse was injected intracerebroventricularly with AAV8-CRH, resulting in overexpression of CRH within the brain to induce a cushingoid phenotype (i.e., hair loss, red skin and obesity). As shown in FIG. 5, one intraperitoneal injection of anti-CRH antibody B (0.3 mg) reversed the observed hair loss.

Example 6—Single Chain Variable Fragments Bind CRH

ScFv constructs offer the advantage of being able to be delivered to the brain via AAV vectors. DNA constructs for ScFv's composed of the heavy and light variable regions of Antibody A and Antibody B, connected by a linker peptide, were generated. The amino acid sequences of the Antibody A and Antibody B scFvs are set forth in SEQ ID NOs: 22 and 23, respectively. DNA constructs were then transfected into Human Embryonic Kidney (HEK) 293t cells and incubated 48 hours. Cells were then lysed and analyzed for CRH binding via a direct CRH ELISA. As shown in FIG. 6, the resulting ScFv's comprising the heavy and light variable regions of Antibody A or Antibody B bound CRH.

Example 7—Humanization of Anti-CRH Antibodies

FIG. 7 provides a comparison between the variable region of anti-CRH Antibody B and a similar human variable framework. Highlighted are the complementarity determining regions (CDRs) of Antibody B. The framework of the variable regions of Antibody B can be altered to match those of the human framework without altering the CDRs of Antibody B.

Example 8—Anti-CRH Antibody Blocked CRHR1 Activation In Vitro

CRHR1 stable overexpressing H4 neuroglioma cells were incubated with combinations of synthetic CRH (Bachem) or purified Antibody B (QED bio) in PBS for 10 minutes. Following treatment cells were lysed in 0.1 M HCl and 1% Triton and then analyzed for cyclic AMP levels via competitive ELISA kit (Thermo Fisher EMSCAMPL). As shown in FIG. 8, Antibody B was able to reduce CRH-induced increases in cyclic AMP.

Example 9—Anti-CRH Antibody Reduced Corticosterone Levels In Vivo

Wildtype (C3B6H) mice were singly housed for 2 months (mild stress). Mice were then treated with varying doses of Antibody B (n=4 per group, sex balanced) and subjected to 30 minutes of acute restraint stress. As shown in FIG. 9, mice treated with Antibody B displayed a clear dose-response type of effect profile (left), and even low doses (1.5 mg/kg) of Antibody B were able to lower baseline corticosterone levels in mice that were singly housed for 2 months.

Example 10—Chronic Variable Stress 2.5 month old wildtype (C3B6) mice were subjected to 2 weeks of chronic variable stress. Two stressors daily×1 hour each. Mice were treated with 25 mg/kg of Antibody B or mouse IgG1 Isotype control (n numbers above, sex balanced). See FIG. 10.

Figure 11A:
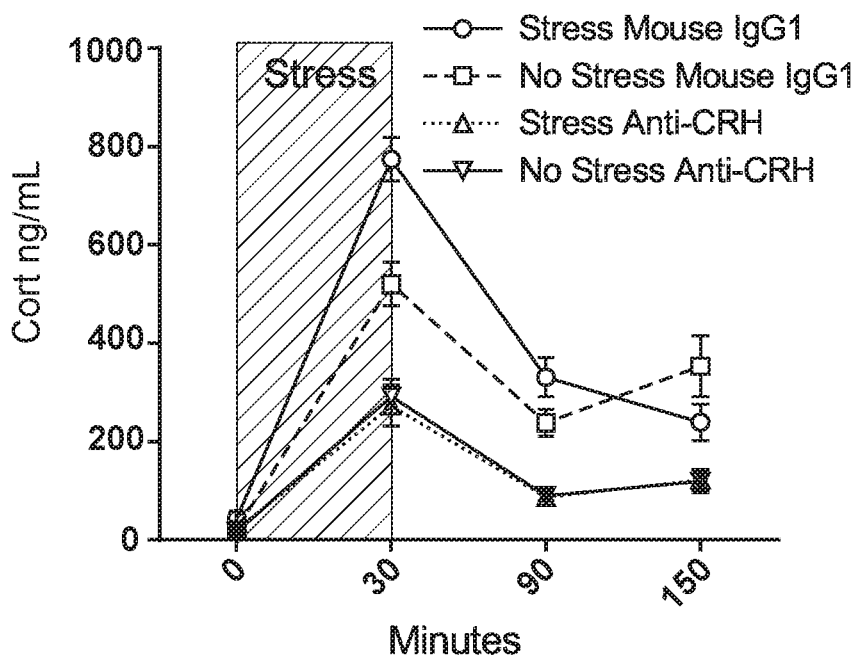
FIG. 11A is a graph showing that treatment with Antibody B (anti-CRH) reduced corticosterone response in mice under chronic stress.
Figure 11B:
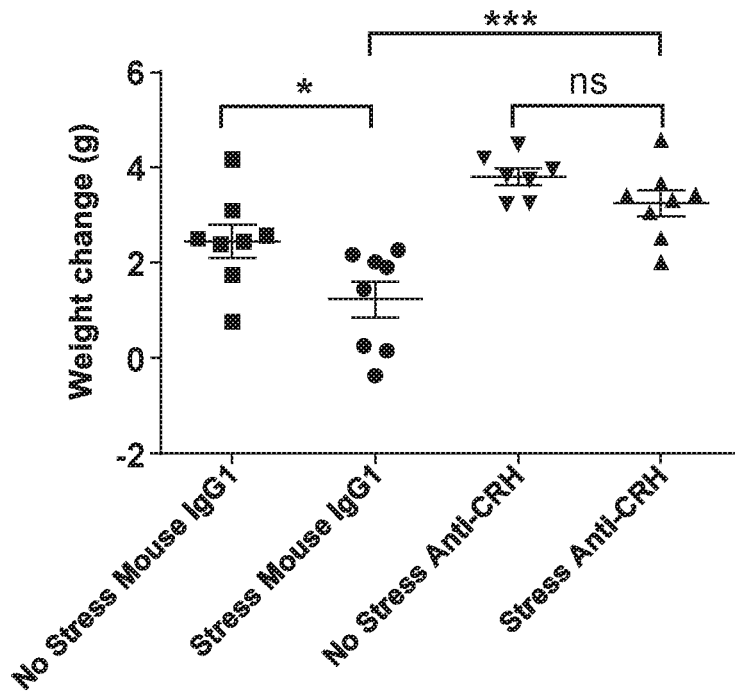
FIG. 11B is a graph showing that mice treated with Antibody B significantly increased weight gain.
Figure 11C:
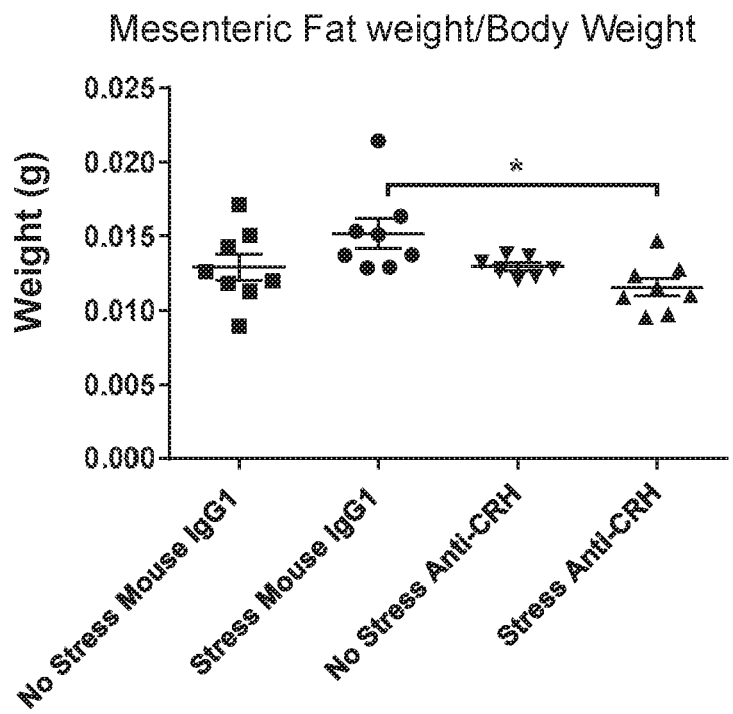
FIGS. 11C and D are graphs showing that treatment with Antibody B (anti-CRH) did not result in increased mesenteric or subcutaneous fat in mice.
Figure 11D:
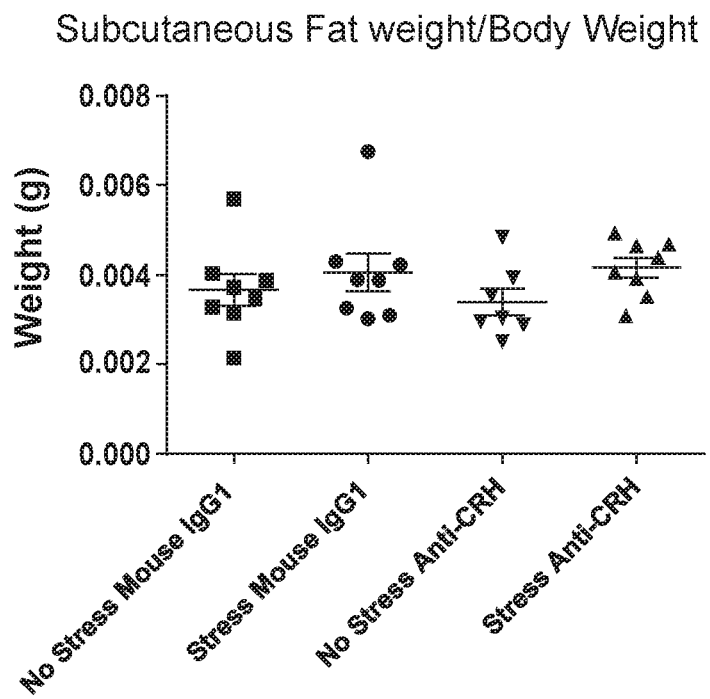
FIGS. 11E, F and G are graphs showing that treatment with Antibody B (anti-CRH) significantly increased spleen cellularity and shifted leukocyte populations to increase B-Cell percentage and decrease T-Cell percentage.
FIGS. 11H and I are graphs showing that Antibody B (anti-CRH) treatment significantly reduced Inflammatory Monocyte cells and NK cells in the spleen of the mice.

As shown in FIG. 11A, treatment with Antibody B suppressed corticosterone response after 2.5 weeks of treatment and 2 weeks of Chronic Variable Stress (CVS). Treatment with Antibody B also significantly increased weight gain in stressed mice (weight gain is appropriate for 2.5 month old mice). See FIG. 10B. Antibody B treatment did not increase subcutaneous fat and significantly decreases Mesenteric (visceral) fat levels. See FIGS. 10C and 10D.

Treatment with Antibody B significantly increased spleen cellularity and shifted leukocyte populations to increase B-Cell percentage and decrease T-Cell percentage (FIGS. 10E, F and G). As shown in FIGS. 10H and 10I, Antibody B treatment significantly reduced Inflammatory Monocyte cells and NK cells in the spleen.

Example 11—Brain RNA Transcriptomics Analysis

Mice (n=6M C57BL/6J Mice) were treated with either Antibody B or mouse IgG1 control antibody for 2.5 weeks—25 mg/kg IP initial injection followed by once weekly IP injection of 12.5 mg/kg.

At the end of the 2.5 weeks, muscle, liver, spleen, and fat were harvested from the mice. Harvested organs were snap-frozen in isopentane chilled on dry ice. Antibody B-treated and control tissues were pulverized under liquid nitrogen using a mortar and pestle and total RNA was extracted with Trizol (Thermo Fisher) reagent. RNA was cleaned-up over a Qiagen RNeasy column with on-column DNase treatment. A subsequent DNase treatment using TURBO DNA-free kit (Ambion) was performed. RNA was quantified using the Qubit 4 fluorometer and the RNA HS assay (Thermo Fisher). RNA quality was determined using the Fragment Analyzer Automated CE System and the Standard Sensitivity RNA Analysis kit (Advanced Analytics). 1 microgram of total RNA was polyA enriched and subjected to library preparation using the TruSeq RNA Sample Prep Kit v2 (Illumina). Libraries were quantified using a library quantification kit (KAPA Biosystems). Library size was determined with the High Sensitivity NGS Fragment Analysis Kit (Advanced Analytics). Libraries were pooled with a strategy to minimize batch effects from library preparation and sequencing and to achieve 30-50M reads per sample.

Figure 12:
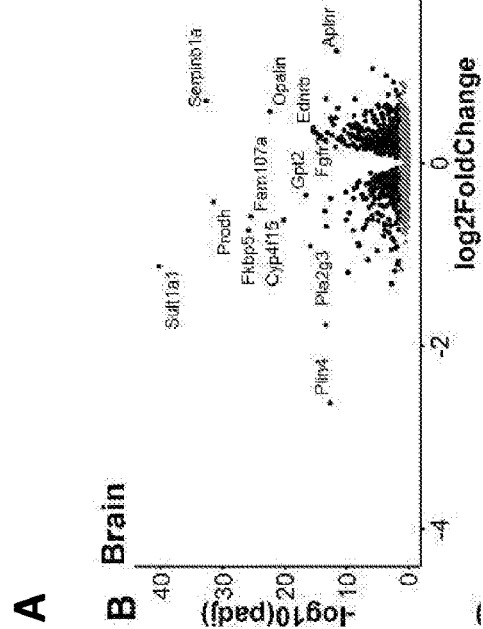
FIGS. 12A and 12B show that brain RNA transcripts are significantly changed in mice treated with Antibody B.
Figure 13A:
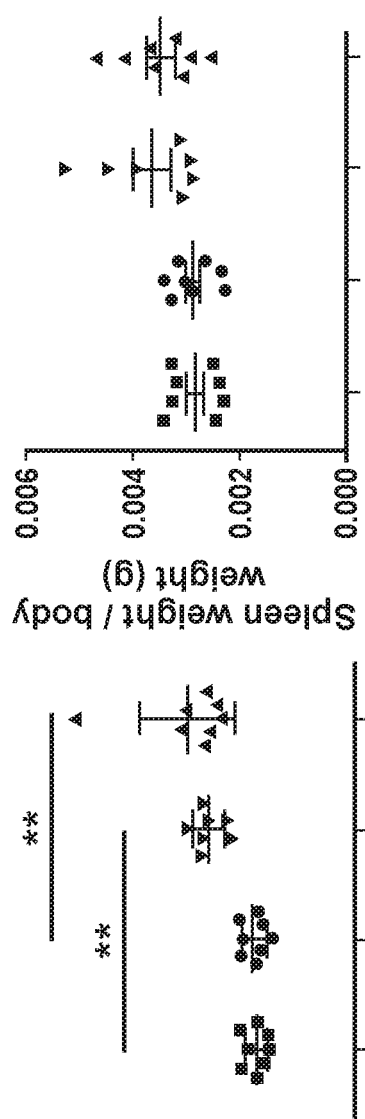
FIGS. 13A-13Q provide the results of the immune profiling performed in Example 12.
Figure 13B:
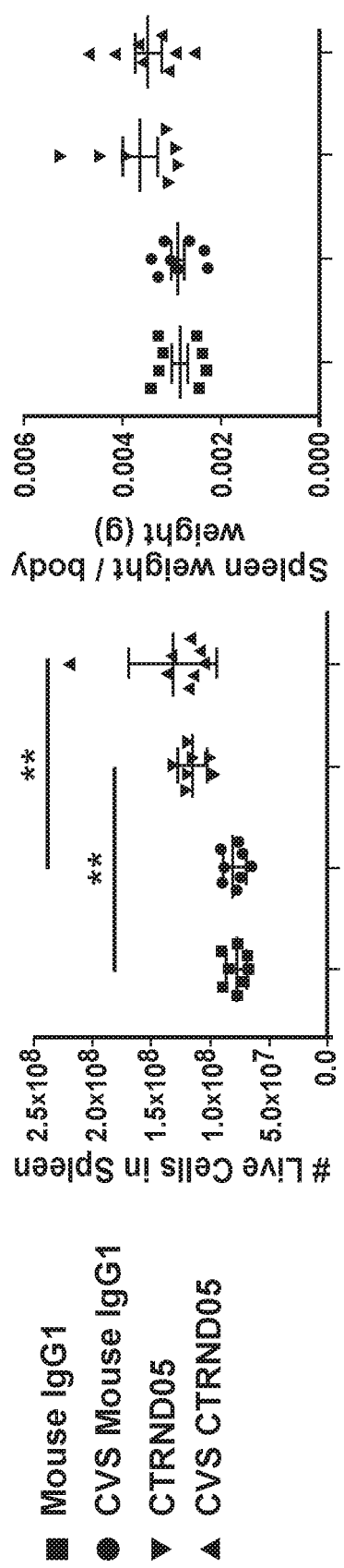
Figure 13C:
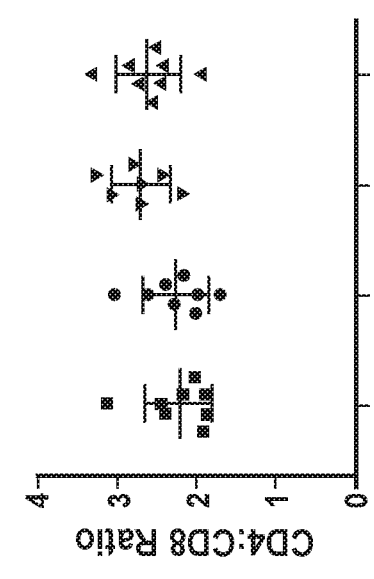
Figure 13D:
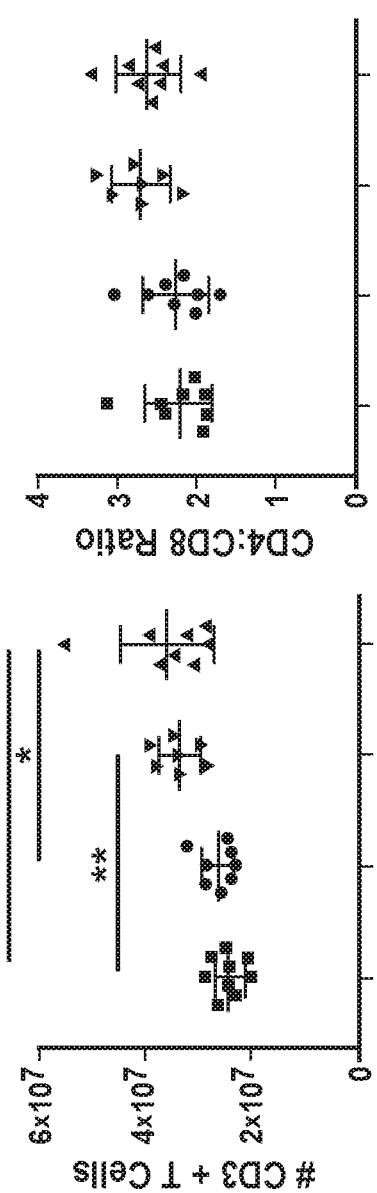
Figure 13E:
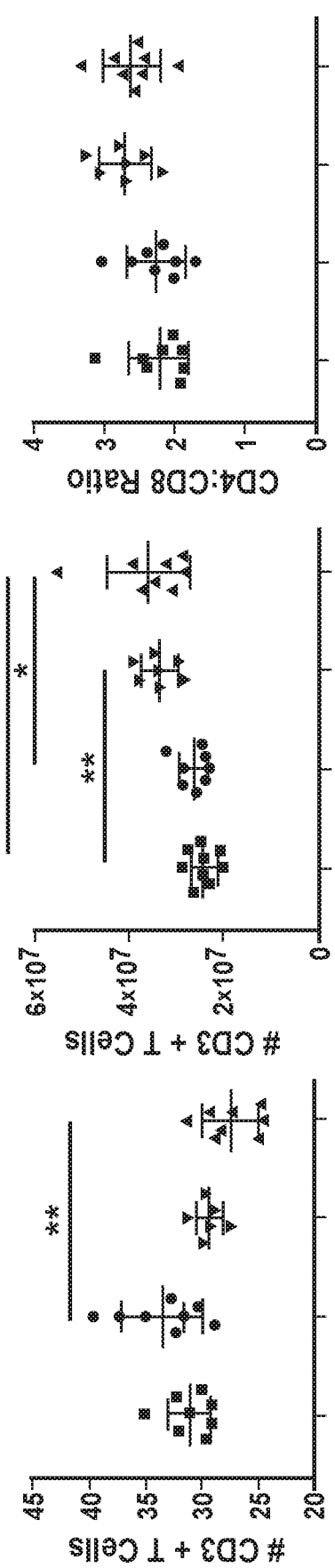
Figure 13N:
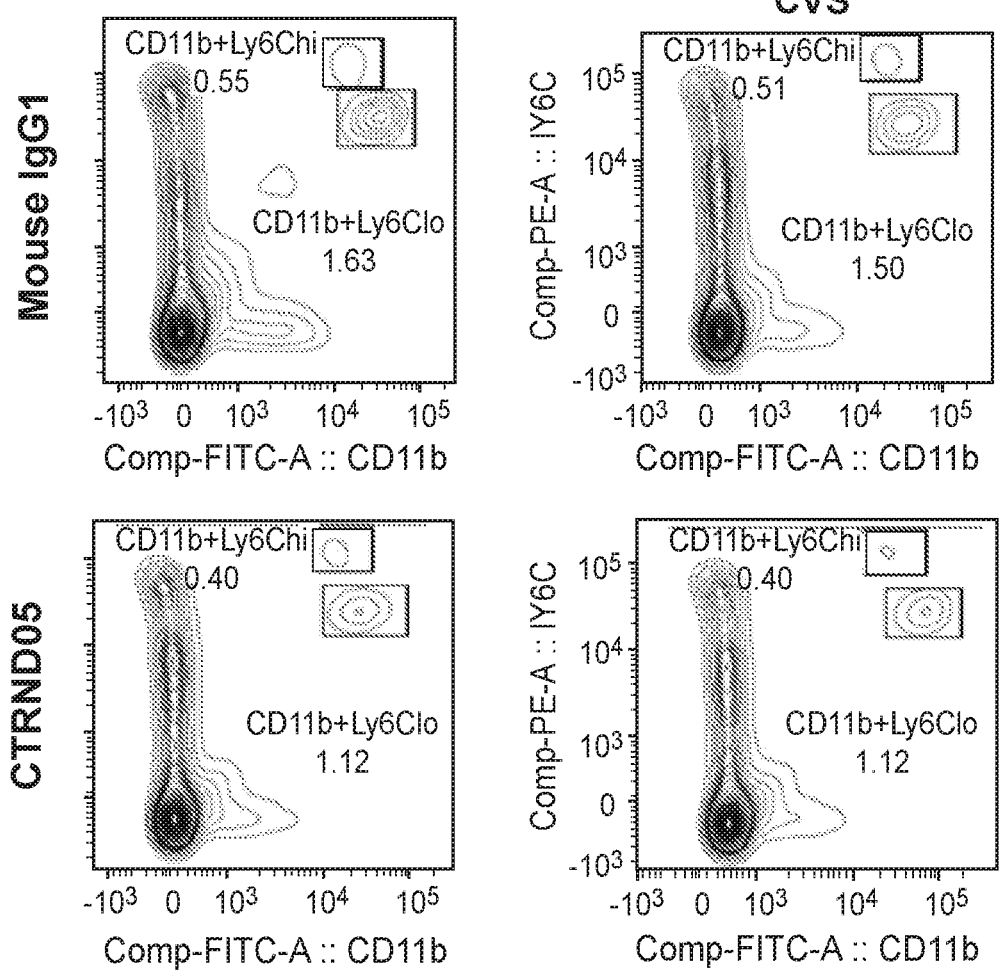
Figure 13O:
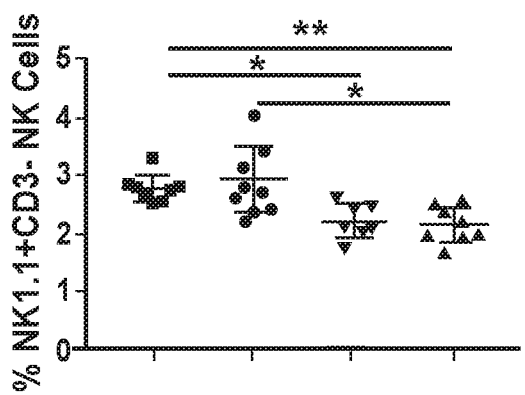
Figure 13P:
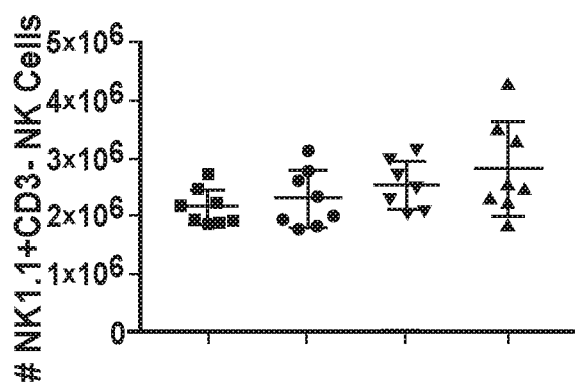
Figure 13Q:
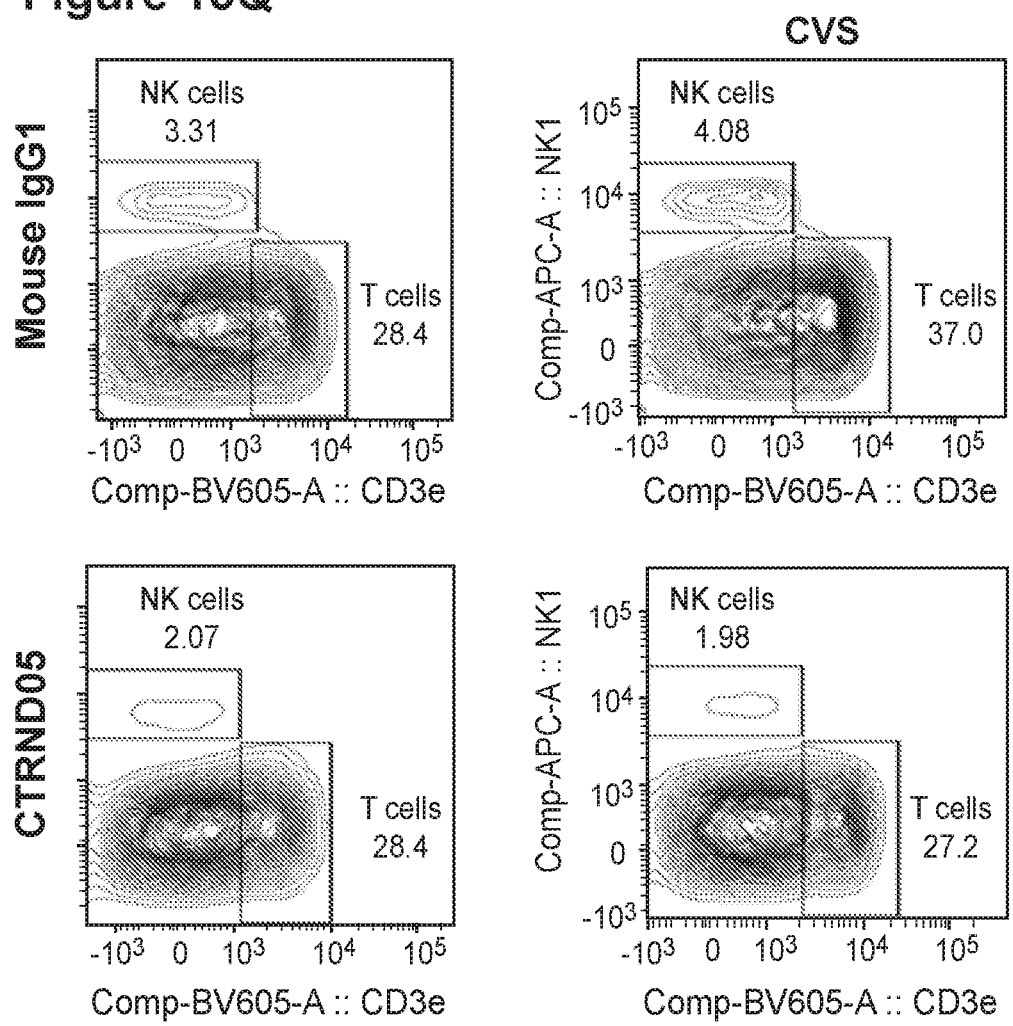

Resulting FASTQ files were aligned against the mouse genome using STAR (Dobin et al., 2013). Subsequent analyses were performed within R version 3.5.1. Differential gene expression analysis will be performed with DESeq2. Changes in gene expression levels between treated versus control groups within each tissue were compared to find differentially expressed genes. Weighted Gene Co-expression Network Analysis (WGCNA) was performed to determine modules of genes with similar expression patterns across samples (Langfelder and Horvath, 2007, 2008). Signed, hybrid networks were detected with WGCNA using a soft power setting (beta) of 6, 4, 6, 4 & 7 for brain, muscle, liver, spleen and fat tissues, respectively. Identification of intramodular hub genes from modules that are significantly correlated with the antibody treatment group were examined and network pathways and gene ontology of genes within significant modules were analyzed using anRichment associated with the WGCNA package. Networks were visualized using the geomnet package within R using the top 20% of genes belonging to each module. See FIG. 12.

Example 12—Immune Profiling

Spleens from the same mice described above in Example 11 (Post 2.5 week treatment with Antibody B) were processed with frosted glass slides and filtered (70 microns) to create single cell suspensions. Red blood cells were lysed with ammonium-chloride-potassium lysis buffer for five minutes on ice and remaining cells were washed with phosphate buffered saline (PBS) prior to staining. $1 \times 10^6$ cells per sample were stained with Fixable Live/Dead Near Infrared Thermofisher (Waltham, Mass., USA) for dead cell exclusion. Cells were incubated with Fc block (2.4G2; BD Biosciences) for five minutes on ice prior to staining with the following antibodies at appropriate concentrations for thirty minutes on ice: CD4-PerCP-Cy5.5 (RM4-5; eBioscience), CD8a-PE-Cy7 (53-6.7; Biolegend), CD3e-BV605 (145-2C11; Biolegend), NK1.1-APC (PK136; eBioscience), CD19-BV711 (6D5; Biolegend), Ly6G-BV421 (1A8; BD Biosciences), Ly6C-PE (HK1.4; eBioscience), CD11b-AF488 (M1/70; eBioscience). Samples were washed once prior to data acquisition on an LSR Fortessa (BD Biosciences) and analysis using FlowJo (v10.5.0; Tree Star). BioLegend (San Diego, Calif., USA). eBioscience (San Diego, Calif., USA). As shown in in FIG. 13, showing the significant increase in the amount of live splenocytes with treatment with Antibody B along with increased B cells and T cells.

Figure 14:
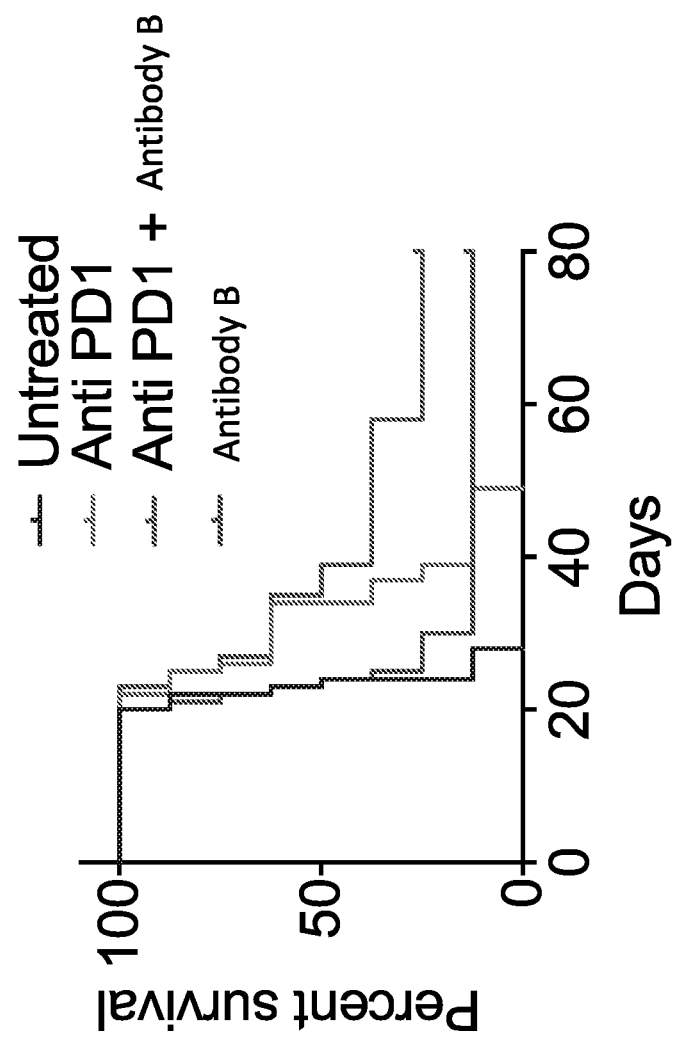
FIG. 14 is a graph showing that treatment with Antibody B increased survival in the GL261 Intracranial mouse glioma model.

Example 13—Treatment with Antibody B Increases Survival in GL261 Intracranial Mouse Glioma Model 10,000 GL261 cells in a 1:1 PBS:methyl cellulose solution were injected intracranially in a volume of 2.5 uL at a point 3 mm below the skull and 2 mm lateral to the bregma using a stereotactic injection in 8-12 week old adult female C57B16/J mice (N=8 per group). Mice were then monitored for progression to humanitarian endpoints as described in UF IACUC 201607966. Treated mice received intraperitoneal injection of 400 ug of anti-PD1 antibody, 400 µg of Antibody B, or both (Clone RMP1-14, BioXCell) five days after tumor implantation, then 200 µg of anti-PD1 and 200 µg of Antibody B every five days for a total of five doses. As shown in FIG. 14, treatment with Antibody B (and combination of Antibody B and anti-PD1 antibody) increased survival in GL261 Intracranial mouse glioma model, surviving more than more than two times longer than untreated animals.

Example 14—Antibody B is Specific for CRF

Direct ELISA where 1 uM (left) or 10 uM (right) of CRF or the CRF-family neuropeptides urocortin (UCN) 1, UCN 2, or UCN 3 were coated to a polycarbonate 96 well ELISA plate. Antibody B was then added at 13.33 nM and incubated for two hours, followed by Anti-Mouse IgG-HRP conjugated detection antibody. ELISA was then developed using TMB reagents and read at 450 nM using a spectrophotometer.

Octet red BLI: Streptavidin probes were bound with UCN 2-BTN and then association and dissociation constants were measured with varying concentrations of Antibody B.

Figure 15:
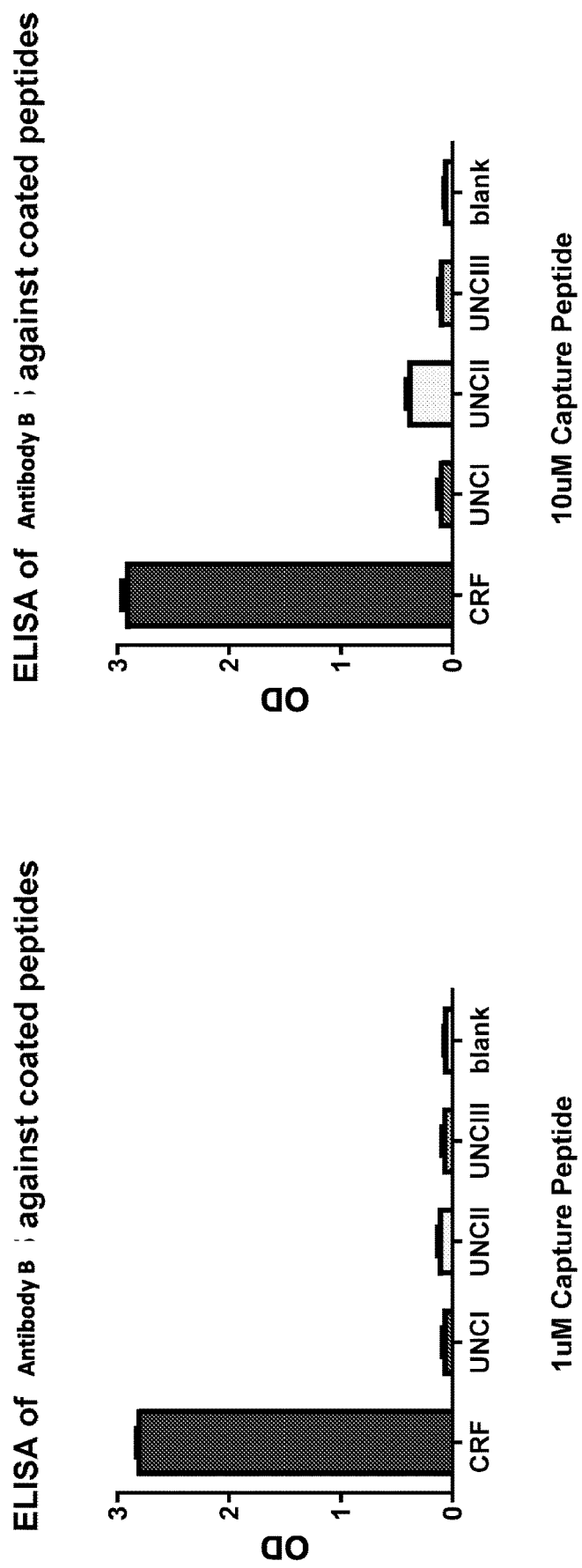
FIG. 15 are graphs showing the results of a direct ELISA demonstrating no cross reactivity of antibody B with UCN 1-3 at 1 μM coat, with a small amount of reactivity for UCN2 coated at 10 μM.

Direct ELISA demonstrated no cross reactivity of Antibody B with UCN 1-3 at 1 uM coat, with a small amount of reactivity for UCN2 coated at 10 uM (FIG. 15).

As shown in FIG. 16, Octet red Biolayer interferometry calculated the dissociation constant of Kd=4.0E-9 for Antibody B to the UCN2 peptide. This affinity is 4000 times lower than the affinity of the Antibody B to CRF peptide. As CRF and UCN2 operate at similar 500 pM-2 nM concentrations in vivo, one would not hypothesize for an appreciable amount of target engagement to occur between UCN2 and Antibody B in vivo.

The entire document is intended to be related as a unified disclosure, and it should be understood that all combinations of features described herein are contemplated, even if the combination of features are not found together in the same sentence, or paragraph, or section of this document. In addition, the disclosure includes, as an additional aspect, all embodiments of the disclosure narrower in scope in any way than the variations specifically mentioned above. With respect to aspects described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature.

All publications, patents and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibody or antigen binding fragment thereof that specifically binds to a region of corticotropin-releasing hormone (CRH), wherein the antibody or antigen binding fragment comprises a set of 6 CDRs set forth in SEQ ID NOs: 12-17.

2. The antibody or antigen binding fragment of claim 1, comprising a heavy chain variable region comprising an amino acid sequence set forth in SEQ ID NO: 19.

3. The antibody or antigen binding fragment of claim 1, comprising a light chain variable region comprising an amino acid sequence set forth in SEQ ID NO: 18.

4. The antibody or antigen binding fragment thereof of claim 1, that is a monoclonal antibody.

5. The antibody or antigen binding fragment of claim 1, that is a humanized antibody.

6. The antibody or antigen binding fragment of claim 1, that is an IgG.

7. The antibody or antigen binding fragment of claim 1, wherein the antigen binding fragment is a Fab fragment or an scFv.

8. The antibody or antigen binding fragment of claim 7, wherein the scFv comprises an amino acid sequence set forth in SEQ ID NO: 22 or SEQ ID NO: 23.

* * * * *